United States Patent
Kiely et al.

(10) Patent No.: US 11,490,643 B2
(45) Date of Patent: Nov. 8, 2022

(54) *LACTOBACILLUS CASEI* FOR TREATING OBESITY AND ASSOCIATED METABOLIC DISORDERS

(71) Applicant: PrecisionBiotics Group Limited, Cork (IE)

(72) Inventors: Barry Kiely, Cork (IE); Eileen Frances Murphy, Cork (IE); Selena Healy, Tipperary (IE)

(73) Assignee: PrecisionBiotics Group Limited, Cork (IE)

( * ) Notice: Subject to any disclaimer, the term of this patent is extended or adjusted under 35 U.S.C. 154(b) by 0 days.

(21) Appl. No.: 17/217,185

(22) Filed: Mar. 30, 2021

(65) Prior Publication Data

US 2021/0282444 A1    Sep. 16, 2021

Related U.S. Application Data

(63) Continuation of application No. 16/060,805, filed as application No. PCT/EP2016/080449 on Dec. 9, 2016, now abandoned.

(30) Foreign Application Priority Data

Dec. 11, 2015    (EP) .................................... 15199657

(51) Int. Cl.

| | | |
|---|---|---|
| *A23L 33/135* | (2016.01) | |
| *C12N 1/20* | (2006.01) | |
| *A61P 1/14* | (2006.01) | |
| *A61P 1/16* | (2006.01) | |
| *A23C 9/123* | (2006.01) | |
| *A61K 35/747* | (2015.01) | |
| *A23L 33/00* | (2016.01) | |
| *C12R 1/245* | (2006.01) | |

(52) U.S. Cl.
CPC .......... *A23L 33/135* (2016.08); *A23C 9/1234* (2013.01); *A23L 33/30* (2016.08); *A61K 35/747* (2013.01); *A61P 1/14* (2018.01); *A61P 1/16* (2018.01); *C12N 1/205* (2021.05); *A23V 2002/00* (2013.01); *A23V 2200/3204* (2013.01); *A23V 2200/332* (2013.01); *A23Y 2220/17* (2013.01); *A23Y 2300/55* (2013.01); *C12R 2001/245* (2021.05)

(58) Field of Classification Search
None
See application file for complete search history.

(56) References Cited

FOREIGN PATENT DOCUMENTS

| | | | |
|---|---|---|---|
| JP | 2009-102270 A | | 5/2009 |
| WO | WO 2007/043933 | * | 4/2007 |
| WO | WO 2007/043933 A1 | | 4/2007 |
| WO | WO 2015/172191 A1 | | 11/2015 |

OTHER PUBLICATIONS

Marteau "Evidence of probiotic stain specificity makes extrapolation of results impossible from a strain to another, even from the same species". Annals of Gastroenterology and Hepatology. 2011, pp. 1-3.*
McFarland et al. "Strain-specificity and disease specificity of probiotic efficacy: a systematic review and meta-analysis". Frontiers in Medicine. 2018, article 124, pp. 1-14.*
Aronsson, L. et al., Decreased Fat Storage By *Lactobacillus paracasei* Is Associated With Increased Levels of Angiopoietin-Like 4 Protein (ANGPTL4), *Plos One*, vol. 5, No. 9, pp. 1-7 (Sep. 2010).
Blüher, M. et al., "Fas And FasL Expression in Human Adipose Tissue is Related to Obesity, Insulin Resistance, and Type 2 Diabetes", *J. Clinical Endocrinology Metabolism*, vol. 99, No. 1, pp. 1-28 (2014).
Carattoli, A. et al., "In Silico Detection and Typing of Plasmids Using PlasmidFinder and Plasmid Multilocus Sequence Typing," *Antimicrobial Agents and Chemotherapy*, vol. 58, No. 7, pp. 3895-3903 (Jul. 2014).
Carver, T. et al., "Artemis and ACT: Viewing, Annotating and Comparing Sequences Stored in a Relational Database," *Bioinformatics*, vol. 24, No. 23, pp. 2672-2676 (Oct. 2008).
Cintra, D.E. et al., "Interleukin-10 is a Protective Factor Against Diet-Induced Insulin Resistance in Liver," *J. Hepatology*, vol. 48, pp. 628-637 (2008).
Cruchet, S. et al., "The Use of Probiotics in Pediatric Gastroenterology: A Review of the Literature and Recommendations by Latin-American Experts," *Pediatric Drugs*, vol. 17, pp. 199-216 (Mar. 2015).
De la Cruz, F., ed., *Horizontal Gene Transfer: Methods And Protocols*, Humana Press, Springer Science + Business Media, 2020 (411 pages).
Den Boer, M.A.M. et al., "Endogenous Interleukin-10 Protects Against Hepatic Steatosis but Does Not Improve Insulin Sensitivity During High-Fat Feeding in Mice," *Endocrinology*, vol. 147, No. 10, pp. 4553-4558 (2006).
Dietrich, C.G. et al., "Commercially Available Probiotic Drinks Containing *Lactobacillus casei*, DN-114001 Reduce Antibiotic-Associated Diarrhea", *World J. Gastroenterology*, vol. 20, No. 42, pp. 15837-15844 (Nov. 2014).
Food and Agriculture Organization of the United Nations and World Health Organization, "Joint FAO/WHO Working Group Report on Drafting Guidelines for the Evaluation Of Probiotics in Food", London Ontario, Canada (Apr. and May 2002) (11 pages).
Holowacz et al. "A multispecies Lactobacillus- and Bifidobacterium-containing probiotic mixture attenuates body weight gain and insulin resistance after a short-term challenge with a high-fat diet in C57/BL6J mice," Pharmanutrition, vol. 3, No. 3, Jul. 2015, pp. 101-107.
International Search Report dated Mar. 14, 2017, in International Application No. PCT/EP2016/080449 (6 pages).

(Continued)

*Primary Examiner* — Vera Afremova
(74) *Attorney, Agent, or Firm* — Bookoff McAndrews, PLLC

(57) ABSTRACT

The strain *Lactobacillus casei* AH077 (NCIMB12019) produces a polysaccharide and increases energy excretion. The strain acts to block fat absorption and is used in the prevention or treatment of obesity and obesity-related metabolic syndrome.

20 Claims, 15 Drawing Sheets

Specification includes a Sequence Listing.

(56) References Cited

OTHER PUBLICATIONS

Lee, I.S. et al., "Shifts in Diet from High Fat to High Carbohydrate Improved Levels of Adipokines and Pro-inflammatory Cytokines in Mice Fed a High-Fat Diet," *Endocrine J.*, vol. 57, No. 1, pp. 39-50 (2010).

Li, X. et al., "oriTfinder: A Web-based Tool for the Identification of Origin of Transfers in DNA Sequences of Bacterial Mobile Genetic Elements," *Nucleic Acids Research*, vol. 46, pp. W229-W234 (May 2018).

Lira, F.S. et al., "Both Adiponectin and Interleukin-10 Inhibit LPS-Induced Activation of the NF-KB Pathway in 3T3-L1 Adipocytes," *Cytokine*, vol. 57, pp. 98-106 (2012).

López, P. et al., "Immune Response To *Bifidobacterium bifidum* Strains Support Treg/Th 17 Plasticity," *PLoS ONE*, vol. 6, No. 9, pp. 1-9, (Sep. 2011).

McFarland, L.V. t al., "Strain-Specificity and Disease-Specificity of Probiotic Efficacy: A Systemac Review and Meta-Analysis," *Frontiers In Medicine*, vol. 5, article 124, pp. 1-14 (May 2018).

Medina, M. et al., "Differential Immunomodulatory Properties of *Bifidobacterium iogum* Strains: Relevance to Probiotic Selection and Clinical Applications," *Clinical And Experimental Immunology*, vol. 150, pp. 531-538 (2007).

Milic, Sandra, et al., "Non-Alcoholic Fatty Liver Disease and Obesity: Biochemical, Metabolic and Clinical Presentations," *World J. Gastroenterology*, vol. 20, No. 28, pp. 9330-9337 (Jul. 2014).

Nerstedt, A. et al., "Administration of *Lactobacillus* Evokes Coordinated Changes in the Intestinal Expression Profile of Genes Regulating Energy Homeostasis and Immune Phenotype in Mice", *British J. Nutrition*, vol. 97, pp. 1117-1127 (2007).

Rutherford, K. et al., "Artemis: Sequence Visualization and Annotation," *Bioinformatics*, vol. 16, No. 10, pp. 944-945 (2000).

Sanders, M.E. et al., "Shared Mechanisms Among Probiotic Taxa: Implications for General Probiotic Claims," *Current Opinion In Biotechnology*, vol. 49, pp. 207-216 (2018).

U.S. FDA, "Conclusion Of The Expert Panel: Determination Of The Gras Status Of The Use Of *Lactobacillus Paracasei*SSP. Paracasei Strain F-19 In Conventional Foods" (Dec. 2018) (83 pages).

\* cited by examiner

1) Unpaired student t-test (Lean versus DIO)
2) One-way ANOVA followed by Tukeys multiple comparison test (DIO versus all strains)

\*\*\* $p<0.001$. \*\* $p<0.01$, \* $p<0.05$.

1) Unpaired student t-test (Lean versus DIO)
2) One-way ANOVA followed by Tukeys multiple comparison test (DIO versus all strains)

* p<0.001,  p<0.01, * p<0.05.

1) Unpaired student t-test (Lean versus DIO)
2) One-way ANOVA followed by Tukeys multiple comparison test (DIO versus all strains)

* $p<0.001$.  $p<0.01$, * $p<0.05$.

1) Unpaired student t-test (Lean versus DIO)
2) One-way ANOVA followed by Tukeys multiple comparison test (DIO versus all strains)
 * $p<0.001$.  $p<0.01$, * $p<0.05$.

1) Unpaired student t-test (Lean versus DIO)
2) One-way ANOVA followed by Tukeys multiple comparison test (DIO versus all strains)
* p<0.001,  p<0.01, * p<0.05.

1) Unpaired student t-test (Lean versus DIO)
2) One-way ANOVA followed by Tukeys multiple comparison test (DIO versus all strains)
* $p<0.001$,  $p<0.01$, * $p<0.05$.

SEQUENCE LISTING

```
<160> NUMBER OF SEQ ID NOS: 3

<210> SEQ ID NO 1
<211> LENGTH: 285
<212> TYPE: DNA
<213> ORGANISM: Lactobacillus casei

<400> SEQUENCE: 1
ttgctggatc acctcctttc taaggaaaca gactgaaagt ctgacggaaa cctgcacaca      60
cgaaactttg tttagttttg aggggatcac cctcaagcac cctaacgggt gcgactttgt     120
tctttgaaaa cctggatatc attgtattaa ttgtttaaa ttgccgagaa cacagcgtat      180
ttgtatgagt ttctgaaaaa gaaattcgca tcgcataacc gctgacgcag tcgacagtat     240
cggttaagtt acaaagggcg cacggtggat gcctttggca ccaga                    285

<210> SEQ ID NO 2
<211> LENGTH: 18
<212> TYPE: DNA
<213> ORGANISM: Unknown
<220> FEATURE:
<223> OTHER INFORMATION: synthesised sequence

<400> SEQUENCE: 2
ctggtgccaa ggcatcca                                                   18

<210> SEQ ID NO 3
<211> LENGTH: 19
<212> TYPE: DNA
<213> ORGANISM: Unknown
<220> FEATURE:
<223> OTHER INFORMATION: synthesised sequence

<400> SEQUENCE: 3
gctggatcac ctcctttct                                                  19
```

LACTOBACILLUS CASEI FOR TREATING OBESITY AND ASSOCIATED METABOLIC DISORDERS

CROSS-REFERENCE TO RELATED APPLICATIONS

This application is a continuation of U.S. application Ser. No. 16/060,805, filed on Jun. 8, 2018, which is the national stage entry of International Application No. PCT/EP2016/080449, filed on Dec. 9, 2016, each incorporated by reference herein in its entirety, PCT/EP2016/080449 claiming priority to European Application No. 15199657.6, filed on Dec. 11, 2015.

SEQUENCE LISTING

This application contains a sequence listing, submitted electronically in ASCII format under the file name 00175-0004-01000_SL.txt, which is incorporated by reference herein in its entirety. The ASCII copy of the sequence listing was created on Mar. 26, 2021, and is 1,205 bytes in size.

INTRODUCTION

The invention relates to a strain of *Lactobacillus casei*.

Obesity is one of the most serious public health challenges of the 21st century. Globally, approximately 13% of adults are obese with a further 39% considered overweight (WHO, 2015). Obesity is a multifactorial disorder which is the result of a long term imbalance between energy intake and expenditure and is influenced by genetic and environmental factors. Obesity is characterized by insulin resistance and a chronic low-grade inflammation (Gregor and Hotamisligil, 2011, Kahn et al., 2006). The intimate interplay between the immune system, metabolism, and gut microbiota may play an important role in controlling obesity and metabolic homeostasis. Obesity increases the risk of developing and exacerbating a cluster of chronic metabolic disorders such as type 2 diabetes (T2DM), non-alcoholic fatty liver disease (NAFLD), hypertension, atherosclerosis, dyslipidemia and cardiovascular disease (Guh et al., 2009) with the prevalence of metabolic comorbidities increasing in-line with increasing BMI (Gupta et al., 2015). Obesity also increases the risk of developing serious and potentially life-threatening diseases such as allergy & asthma, osteoarthritis, gallbladder disease and Non-alcoholic steatohepatitis (NASH), a condition in which fat builds up in the liver and major cause of cirrhosis of the liver.

Metabolic syndrome, an increasingly common condition, refers to the combination of obesity, hyperlipidemia (high triglycerides), hypertension (high blood pressure) and glucose intolerance (high blood sugar) and low HDL cholesterol. These risk factors assist in identifying subjects at high risk of developing type 2 diabetes (T2D) and cardio-vascular disease.

Non-alcoholic fatty liver disease (NAFLD) is a very common disorder and refers to a group of conditions where there is accumulation of excess fat in the liver of people who drink little or no alcohol.

The more severe form of NAFLD is called non-alcoholic steatohepatitis (NASH). NASH causes the liver to swell and become damaged. NASH tends to develop in people who are overweight or obese, or have diabetes, high cholesterol or high triglycerides.

A large body of clinical and experimental data shows that increased flux of free fatty acids from increased visceral adipose tissue can lead to NAFLD related with insulin resistance. Thus, individuals with obesity, insulin resistance, and dyslipidemia are at the greatest risk of developing NAFLD.

Since the observation that germ-free mice were found to be leaner than their conventionally-raised counterparts (Backhed et al., 2004) the contribution of the gut microbiota to the development of obesity is increasingly being investigated (Backhed et al., 2007, Cani et al., 2008b, Ridaura et al., 2013, Vrieze et al., 2012). The contribution of the gut microbiota to obesity is multifactorial and involves issues such as enhanced energy harvest and fat storage (Turnbaugh et al., 2006) altered metabolic pathways (Kotzampassi et al., 2014, Turnbaugh et al., 2009) and bacterial translocation leading to chronic low-grade inflammation (Cani et al., 2007, Cani et al., 2008a). The manipulation of gut microbiota by probiotics is therefore a potential therapeutic tool to help ameliorate obesity and improve metabolic health. *Lactobacillus* strains are commonly used as probiotics and have a body of evidence that supports heath benefit effects in vivo in a strain specific manner (Aronsson et al., 2010, Lee et al., 2006, Naito et al., 2011).

The mechanism of action of these strains are not well characterised. One group of molecules that are of interest are bacterial exopolysaccharides (EPS). EPS's are high-molecular-weight polymers that are composed of sugar residues and are secreted by bacteria into the surrounding environment. Exopolysaccharide (EPS)-producing bacteria have been shown to have immunomodulatory effects (Fanning et al., 2012, Hidalgo-Cantabrana et al., 2014, Vinderola et al., 2006, Volman et al., 2008, Jones et al., 2014). Many lactic acid bacteria (LAB) have the ability to synthesize EPS. However, EPS are heterogeneous molecules and differ in composition, charge and molecular structure which may account for the strain-specific bioactivity observed (Adams et al., 2008, Bland et al., 2004, Hidalgo-Cantabrana et al., 2012, Kankainen et al., 2009). The chronic low-grade inflammation associated with obesity and metabolic disorders (Gregor and Hotamisligil, 2011) is one risk factor that could be targeted for manipulation by administration of probiotics to favourably influence the development of obesity. We have previously shown that another lactic acid bacterium, *B. longum* NCIMB41003, has anti-inflammatory effects. This bacterium has a substantial EPS coat. The EPS material also has an anti-inflammatory effect as described in WO2010055499A.

STATEMENTS OF INVENTION

The invention provides the deposited strain NCIMB 42019. A strain of *Lactobacillus casei* AH077 was deposited with the NCIMB under accession number 42019 on Aug. 2, 2012, under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK. The microorganism produces a polysaccharide and increases energy excretion.

The strain of the invention may be used for reducing body fat accumulation in a subject. The strain may have the action of blocking fat absorption from the intestinal tract. The strain may be used for blocking weight gain or reducing weight. The strain may be used for the treatment, prevention, or alleviation of a condition resulting from excessive body fat accumulation.

The strain is particularly useful in the prevention or treatment of obesity and obesity-related metabolic syndrome.

The strain may be in the form of viable cells. The strain may be in the form of non-viable cells. The general use of probiotic bacteria is in the form of viable cells. However, use can also be extended to non-viable cells such as killed cultures, mixtures of viable and non-viable cultures or compositions containing beneficial factors expressed by the probiotic bacteria. This could include thermally killed micro-organisms or micro-organisms killed by exposure to altered pH or subjection to pressure or gamma irradiation. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

The invention also provides a formulation which comprises a strain as described herein. The formulation may further comprise a probiotic material. The formulation may further comprise a prebiotic material. The formulation may further comprise an ingestible carrier. The ingestible carrier may a pharmaceutically acceptable carrier such as a capsule, tablet or powder. The ingestible carrier may be a food product such as acidified milk, yoghurt, frozen yoghurt, milk powder, milk concentrate, cheese spreads, dressings or beverages. The formulation may further comprise a protein and/or peptide, in particular proteins and/or peptides that are rich in glutamine/glutamate, a lipid, a carbohydrate, a vitamin, mineral and/or trace element. The *Bifidobacterium* strain may be present in an amount of more than $10^6$ cfu per gram of the formulation. The formulation may further comprise an adjuvant. The formulation may further comprise a bacterial component. The formulation may further comprise a drug entity. The formulation may further comprise a biological compound. The formulation may be used for immunisation and vaccination protocols.

The invention also provides a freeze dried composition comprising a strain of the invention or a formulation of the invention.

The invention also provides a strain or a formulation as described herein for use in foodstuffs.

The invention also provides a strain or a formulation as described herein for use as a medicament The invention also provides a capsule comprising a strain or a formulation of the invention.

The composition, such as a capsule, may be adapted for controlled release in the gastrointestinal tract.

The invention also provides a strain or a formulation as described herein for use in the prophylaxis and/or treatment of obesity and related illnesses.

The invention also provides a strain or a formulation as described herein for use in the prophylaxis and/or treatment of non-alcoholic fatty liver disease (NAFLD).

Strains as described herein may be used in the preparation of a panel of biotherapeutic agents for modifying the levels of IL-10.

The invention also provides a strain or a formulation as described herein for use in the prophylaxis and/or treatment of obesity related inflammation.

The invention also provides a strain or a formulation as described herein for use in the prophylaxis and/or treatment of obesity related metabolic dysregulation.

The invention also provides a method for blocking fat absorption, comprising administering a composition comprising a strain deposited with the NCIMB under accession number NCIMB 41715 to a subject in need of blocking fat absorption.

The invention further provides a method for preventing or treating obesity, comprising administering a composition comprising a strain deposited with the NCIMB under accession number NCIMB 41715 to a subject in need of preventing or treating obesity.

Also provided is a method for preventing or treating obesity-related metabolic syndrome, comprising administering a composition comprising a strain deposited with the NCIMB under accession number NCIMB 41715 to a subject in need of preventing or treating obesity-related metabolic syndrome.

The invention also provides a method for preventing or treating Non-alcoholic fatty liver disease (NAFLD), comprising administering a composition comprising a strain with the NCIMB under accession number NCIMB 41715 to a subject in need of preventing or treating Non-alcoholic fatty liver disease (NAFLD).

It will be appreciated that the specific strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

The invention also includes mutants and variants derived from the strain of the invention, whilst still having the activity of the deposited strain. The mutants, variants include a strain whose genetic and/or phenotypic properties are altered compared to the parent strain. A naturally occurring variant includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

A person skilled in the art would appreciate that mutant or variant strains of can be identified by DNA sequence homology analysis with the parent strain. Strains of having a close sequence identity with the parent strain without demonstrable phenotypic or measurable functional differences are considered to be mutant or variant strains. A strain with a sequence identity (homology) of 99.5% or more with the parent DNA sequence may be considered to be a mutant or variant. Sequence homology may be determined using on-line homology algorithm "BLAST" program, publicly available at http://www.ncbi.nlm.nih.gov/BLAST/.

Mutants of the parent strain also include derived strains having at least 95.5% sequence homology to the 16s-23s intergenic spacer polynucleotide sequence of the parent strain. These mutants may further comprise DNA mutations in other DNA sequences in the bacterial genome.

BRIEF DESCRIPTION OF THE FIGURES

The invention will be more clearly understood from the following description of some embodiments thereof, given by way of example only, with reference to the accompanying figures, in which.

DETAILED DESCRIPTION OF THE INVENTION

Figure 1:
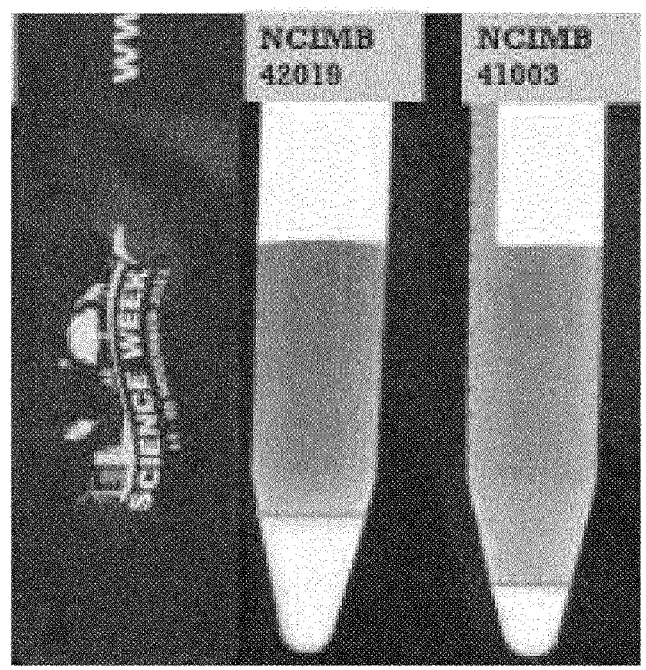
FIG. 1 shows strain bulkiness of *L. casei* NCIMB 42019 and *B. longum* NCIMB 41003 as measured by EPS fluffy pellet height.

A deposit of *Lactobacillus* strain AH077 was made at the National Collections of Industrial and Marine Bacteria Limited (NCIMB) Ferguson Building, Craibstone Estate, Bucksburn, Aberdeen, AB21 9YA, Scotland, UK on Aug. 2, 2012 and accorded the accession number NCIMB 42019.

This specification also makes reference by way of comparison to the strain *Bifidobacterium longum* 35624 which is deposited at the National Collections of Industrial and Marine Bacteria Limited (NCIMB) Ferguson Building, Craibstone Estate, Bucksburn, Aberdeen, AB21 9YA, Scotland, UK on Jan. 13, 1999 under accession number NCIMB 41003.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

We have found that a novel EPS-producing *Lactobacillus* strain (*L. casei* AH077) attenuated markers associated with obesity and associated metabolic disorders. *L. casei* AH077 administration was associated with alteration of gut microbiota, decreased fat storage and decreased hepatic triglyceride and hepatic total cholesterol levels and increased fat excretion. Surprisingly, administration of *B. longum* NCIMB41003 did not have the same effect.

Example 1—Identity of *L. casei* NCIMB 42019 was Confirmed by BLAST Analysis of the Intergenic Spacer (IGS) Region Method 16s-23s intergenic spacer (IGS) sequencing was performed to identify *L. casei* NCIMB 42019. Briefly, total DNA was isolated from the strains using 100 µl of Extraction Solution and 25 µl of Tissue Preparation solution (Sigma-Aldrich, XNAT2 Kit). The samples were incubated for 5 minutes at room temperature followed by 2 h at 95° C. and then 100 µl of Neutralization Solution (Sigma-Aldrich, XNAT2 kit) was added. DNA solution was quantified using a Nanodrop spectrophotometer and stored at 4° C. PCR was performed using the IGS primers. The primer pairs used for identification of the both strain were IGS R 5'-CTGGTGC-CAAGGCATCCA-3' and IGS L 5'-GCTGGAT-CACCTCCTTTCT-3'. The cycling conditions were 94° C. for 4 min (1 cycle), 94° C. for 45 sec, 53° C. for 45 sec, 72° C. for 45 sec (28 cycles). The PCR reaction contained 2 µl (100 ng) of DNA, PCR mix (Sigma-Aldrich, Red Taq), 0.025 nM IGS L and R primer (MWG Biotech, Germany). The PCR reactions were performed on an Eppendorf thermocycler. The PCR products were run alongside a molecular weight marker (100 bp Ladder, Roche) on a 2% agarose EtBr stained gel in TAE, to determine the IGS profile. PCR products of *Bifidobacterium* (single band) were purified using the Promega Wizard PCR purification kit. PCR products of *Lactobacillus* yield 3 bands. The band present at approx. 280 bp (lowest band) was excised, purified using the GenElute Agarose Spin Column (Sigma-Aldrich) and re-sequenced as above and the PCR product was purified using the Promega Wizard PCR purification kit. The purified PCR products were sequenced at Beckman Coulter Genomics (UK) using the primer sequences (above) for the intergenic spacer region. Sequence data was then searched against the NCBI nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/) to identify the nearest match to the sequence.

Results

Identity of *L. casei* NCIMB 42019 was Confirmed by BLAST Analysis of the Intergenic Spacer (IGS) Region.

TABLE 1

Blast results of the intergenic spacer (IGS) region of *L. casei* NCIMB 42019.

| Sample | Accession no | Closest Match on NCBI BLAST Jul. 12, 2015 | Identities | % Match | bp |
|---|---|---|---|---|---|
| NCIMB 42019 | gb(CP012148.1) | *Lactobacillus paracasei* strain L9, complete genome | 272/280 | 97% | 285 |
| | gb(CP001084.2) | *Lactobacillus casei* str. Zhang, complete genome | | | |

TABLE 2

Sequence of the intergenic spacer (IGS) region of *L. casei* NCIMB 42019.

| IGS Sequence of *L. casei* NCIMB 42019 (285 nt) | TTGCTGGATCACCTCCTTTCTAAGGAAACAGACTGAA AGTCTGACGGAAACCTGCACACACGAAACTTTGTTTA GTTTTGAGGGGATCACCCTCAAGCACCCTAACGGGTG CGACTTTGTTCTTTGAAAACCTGGATATCATTGTATT AATTGTTTTAAATTGCCGAGAACACAGCGTATTTGTA TGAGTTTCTGAAAAAGAAATTCGCATCGCATAACCGC TGACGCAGTCGACAGTATCGGTTAAGTTACAAAGGGC GCACGGTGGATGCCTTTGGCACCAGA |
|---|---|

Example 2—EPS Fluffy Pellet Test (Strain Bulkiness)

Method

Each strain was fermented in a broth. The particulate collected after centrifugation was washed and subsequently freeze dried.

The freeze dried powder, adjusted for total cell number (2×10E10), was re-suspended in 10 ml PBS and centrifuged at 4000 rpm/10 mins/4° C.

Results

FIG. 1: Strain bulkiness of *L. casei* NCIMB 42019 and *B. longum* NCIMB 41003 as measured by EPS fluffy pellet height.

*B. longum* NCIMB 41003 produced a 0.9 cm fluffy pellet while *L. casei* NCIMB 42019 produced a 1.6 cm fluffy pellet.

Conclusion

*B. longum* NCIMB 41003 is known to be a high EPS producer. The EPS fluffy pellet test, and the resulting pellet height, confirms that the strains are EPS producers, with some strains producing more than others.

Example 3—Microbial Adhesion to Hexadecane (MATH) Assay

Hydrophobicity is the physical property of a molecule whereby it repels water. Hydrophobic materials are used for oil removal from water, the management of oil spills, and chemical separation processes to remove non-polar substances from polar compounds. Hydrophobicity of a bacterial cell depends on the composition of its cell surface with respect to the proteins, peptides and polysaccharides present. The ability of a probiotic strain to adhere to the intestinal mucosa helps the bacterial cell to establish itself during gastrointestinal transit providing it with a competitive advantage in the intestine. Hydrophobicity of a strain is one factor contributing to adhesive ability. The determination of bacterial adhesion to hexadecane as an indication of the strains ability to adhere to intestinal epithelial cells is a valid qualitative approach (Kiely & Olson, 2000).

Method

The ability of *L. casei* NCIMB 42019 and an EPS low *Lactobacillus* strain to adhere to hexadecane as a measure of their hydrophobicity was determined using the microbial adhesion to hexadecane (MATH) test. Adhesion to hexadecane was measured according to the method of Rosenberg et al, 1980 with some modifications (Crow and Gopal, 1995; Bellon-Fontaine et al, 1996). Bacteria were harvested in the stationary phase by centrifugation at 5000 g for 15 min, washed twice with PBS, and resuspended in 0.1 mol/l $KNO_3$ (pH 6.2) to an $OD_{600}$ of 0.8. The absorbance of the cell suspension was measured at 600 nm (A0). 2 ml of hexadecane (Sigma Aldrich) was added to 2 ml of cell suspension. After 10 min pre-incubation at room temperature, the two-phase system was mixed by vortexing for 2 mins. The aqueous phase was removed after 20 min of incubation at room temperature, and its absorbance at 600 nm (A1) was measured. The % of bacterial adhesion to hexadecane was calculated as $(1-A1/A0)\times 100$, where A0 and A1 are the absorbance before and after extraction with the solvents, respectively. Experiments were done in triplicate with cells coming from independent cultures.

Results

Figure 2:
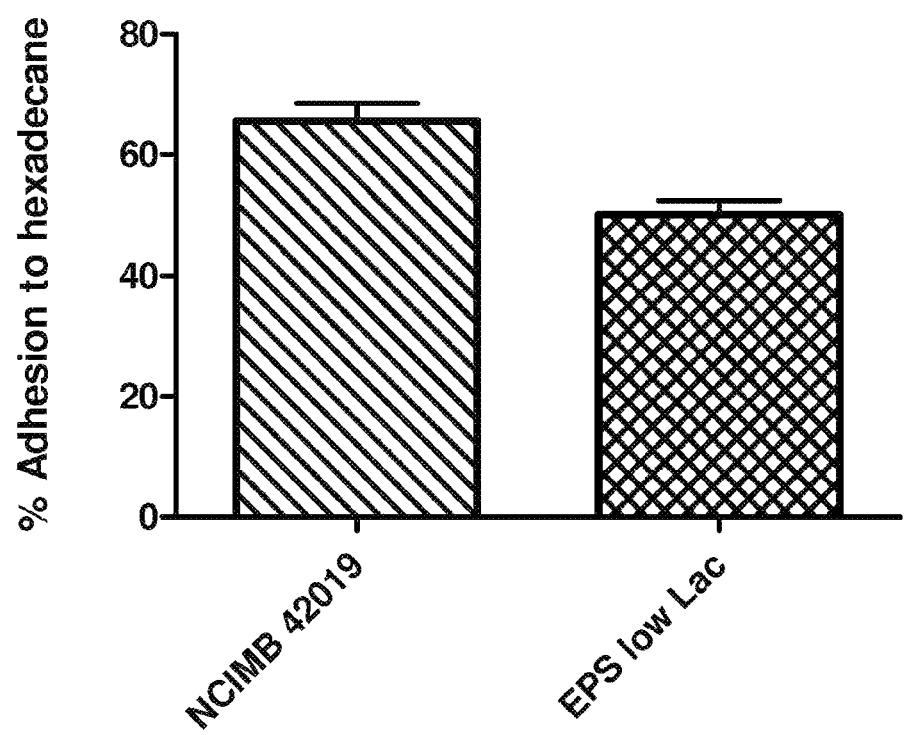
FIG. 2 is a bar chart of % adhesion to hexadecane of *L. casei* NCIMB 42019 and an EPS low *Lactobacillus* strain.

FIG. 2: % adhesion of *L. casei* NCIMB 42019 and an EPS low *Lactobacillus* strain to hexadecane as a measure of their hydrophobicity.

Conclusion

*L. casei* NCIMB 42019 (65.6%) showed a higher affinity for hexadecane, indicating that it had greater hydrophobicity, in comparison to an EPS low *Lactobacillus* strain (50.2%).

Example 4—Fat Binding Capacity

The ability of *L. casei* NCIMB 42019 and a low EPS producing strain to bind fat in vitro was investigated.

Method $5\times 10^{10}$ cells of *L. casei* NCIMB 42019 and $5\times 10^{10}$ cells of EPS low *Lactobacillus* strain were mixed with 10 ml of PBS. 10 ml of olive oil was then added. The mixture was vortexed thoroughly and incubated at 37° C. with shaking. After 2 hr incubation the mixture was centrifuged at 675 g for 10 mins. The unbound layers of fat (top layer), as an indication of the fat binding capacity of the strains, were compared visually. A commercially available fat-binder (XLS Medical) containing the active ingredient Litramine™ was included (2 g sachet+10 ml PBS+10 ml olive oil). A control containing 10 ml PBS and 10 ml olive oil only was also included.

Results

Figure 3:
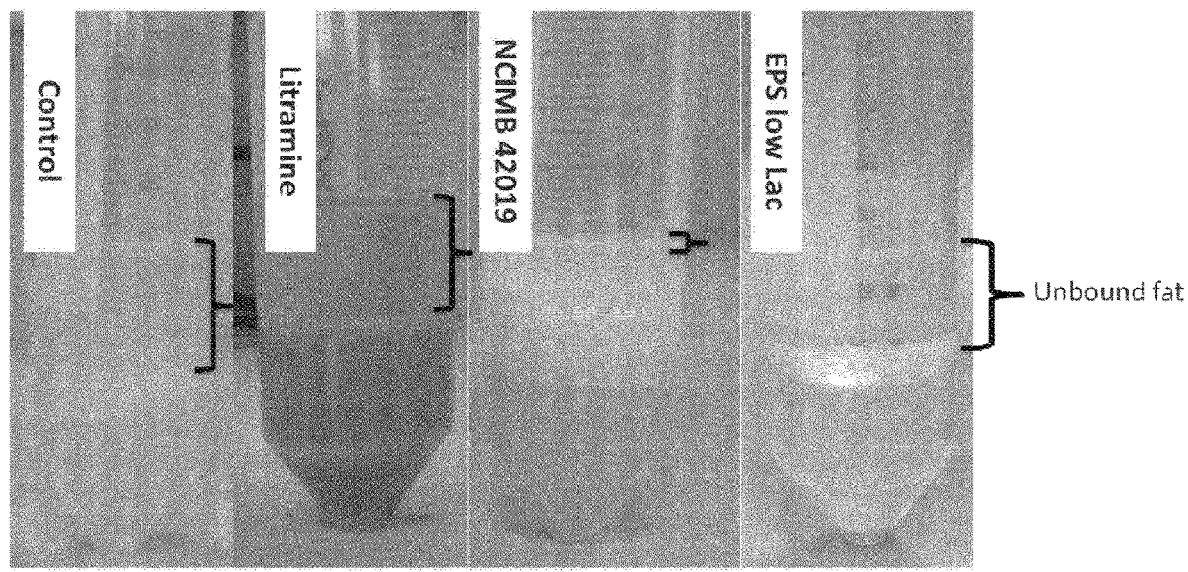
FIG. 3 is a photograph showing the fat binding capacity of *L. casei* NCIMB 42019 and a low EPS producing strain to bind fat in vitro compared the commercially available XLS Medical fat binder containing Litramine™.

FIG. 3 shows the unbound layer of fat is clearly visible as the top layer for all samples. The unbound fat layer observed for *L. casei* NCIMB 42019 is significantly smaller than the unbound fat layer observed for the EPS low *Lactobacillus* strain and the negative and positive controls.

Conclusion

In comparison to the EPS low *Lactobacillus* strain and the commercially available XLS Medical fat-binder *L. casei* NCIMB 42019 demonstrates an increased capacity to bind to fat in vitro.

Example 5—PBMC Anti-Inflammatory Profiles

The anti-inflammatory profile of *L. casei* NCIMB 42019 and *B. longum* NCIMB 41003 were examined by assessing the induction of the anti-inflammatory cytokine IL-10 and the pro-inflammatory cytokine TNF-α in the peripheral blood mononuclear cell (PBMC) cytokine induction assay.

Method

Peripheral Blood Mononuclear Cell (PBMC) Cytokine Induction Assay

Blood was obtained from three healthy volunteers under approval of the Clinical Research Ethics Committee of the Cork Teaching Hospitals. Subjects were all and had abstained from probiotic, antibiotic or anti-inflammatory medication usage for one month or longer prior to blood donation. PBMCs were extracted from whole blood by density gradient separation using histopaque (Sigma-Aldrich), a hydrophilic polysaccharide that separates layers of blood, with a 'buffy/coat' forming under a layer of plasma which contains the PBMCs. For each strain, 100 mg of freeze-dried powder was weighed out and re-suspended in sterile Dulbecos PBS (Sigma-Aldrich). The bacterial cells were washed twice by centrifugation (4000 rpm/10 min/4° C./Brake 0) and re-suspended in sterile PBS. Direct microscopic counts were performed and the cell preparations were diluted to the appropriate concentrations to give a ratio of 100:1; 50:1; 25:1 total bacteria:PBMC cells. Technical replicates were performed in triplicate. PBMCs were then incubated at a concentration of $2\times 10^5$ cells/ml for 48 h at 37° C. (in the presence of penicillin and streptomycin (Sigma-Aldrich)) with control media, or with increasing concentrations of the bacterial strains: $1\times 10^6$ cells/ml (25:1 Bacterial:PBMC), $1\times 10^7$ cells/ml (50:1 Bacteria:PBMC) and $2\times 10^7$ cells/mL (100:1 Bacteria:PBMC). Supernatants were assayed for the anti-inflammatory cytokine IL-10 and the pro-inflammatory cytokine TNF-α which were measured using the MesoScale Discovery (MSD) multiplex platform tissue culture kits (Meso Scale Diagnostics, Maryland, USA). *B. longum* NCIMB 41003, which has previously been shown to have anti-inflammatory activity (Groeger et al., 2013) was used as a positive control to validate the accuracy of the assay.

Results

Figure 4:
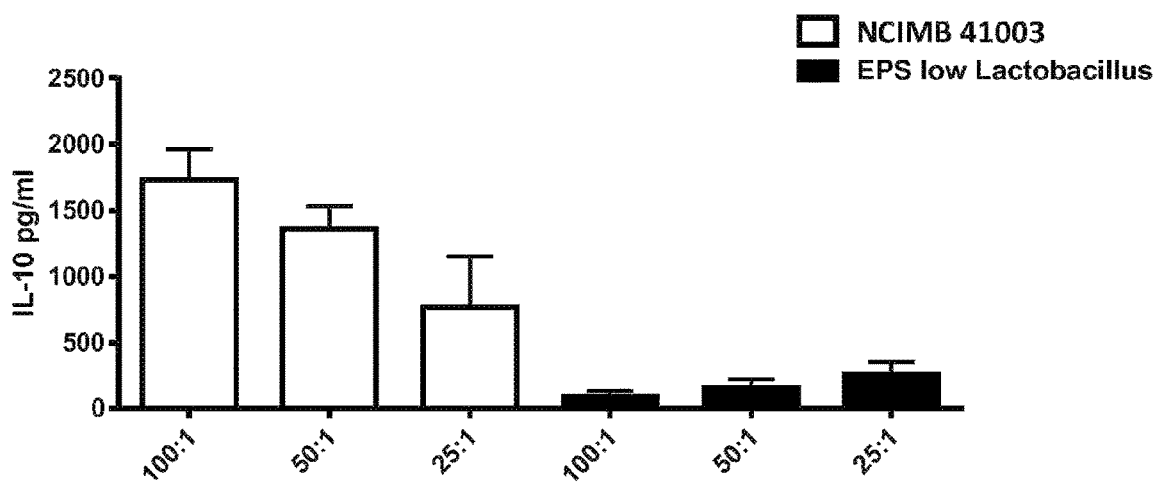
FIG. 4 is a chart of IL-10 induction in the PBMC cytokine induction assay following 48 h stimulation with the EPS+ve *B. longum* NCIMB 41003 and a low EPS producing *Lactobacillus* strain. There is an enhanced induction of the anti-inflammatory cytokine IL-10 following stimulation with the EPS+ve *B. longum* NCIMB 41003 relative to the EPS low *Lactobacillus* strain.

FIG. 4: IL-10 induction in the PBMC cytokine induction assay following 48 h stimulation with the EPS+ve *B. longum* NCIMB 41003 and a low EPS producing *Lactobacillus* strain. There is an enhanced induction of the anti-inflammatory cytokine IL-10 following stimulation with the EPS+ve *B. longum* NCIMB 41003 relative to the EPS low *Lactobacillus* strain.

Figure 5:
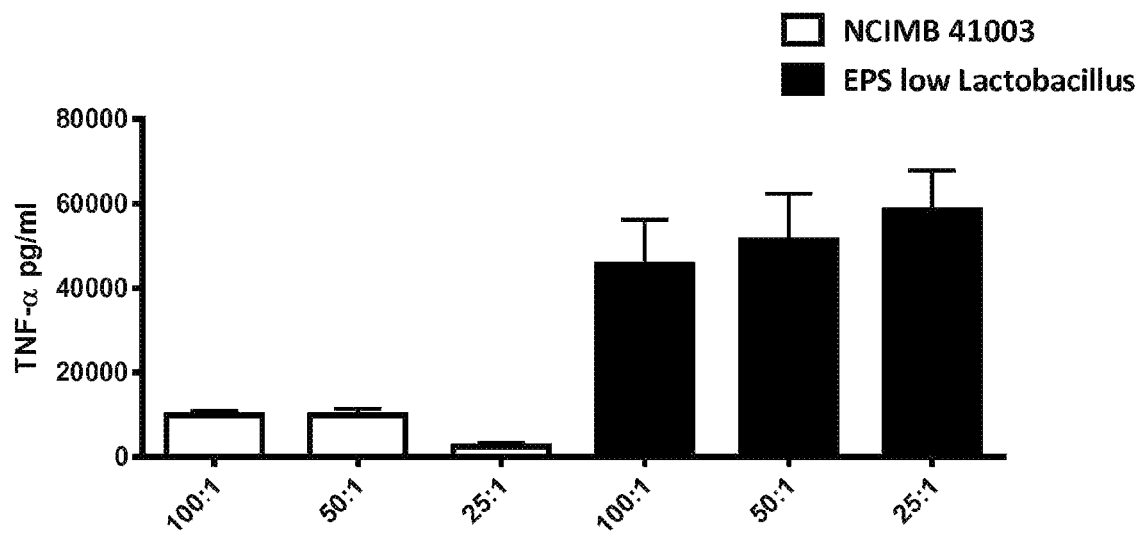
FIG. 5 is a chart of TNF-α induction in the PBMC cytokine induction assay following 48 h stimulation with *B. longum* NCIMB 41003 and a low EPS producing *Lactobacillus* strain. There is a decreased induction of the pro-inflammatory cytokine TNF-α induction following stimulation with the EPS+ve *B. longum* NCIMB 41003 relative to the EPS low *Lactobacillus* strain.

FIG. 5: TNF-α induction in the PBMC cytokine induction assay following 48 h stimulation with *B. longum* NCIMB 41003 and a low EPS producing *Lactobacillus* strain. There is a decreased induction of the pro-inflammatory cytokine TNF-α induction following stimulation with the EPS+ve *B. longum* NCIMB 41003 relative to the EPS low *Lactobacillus* strain.

Figure 6:
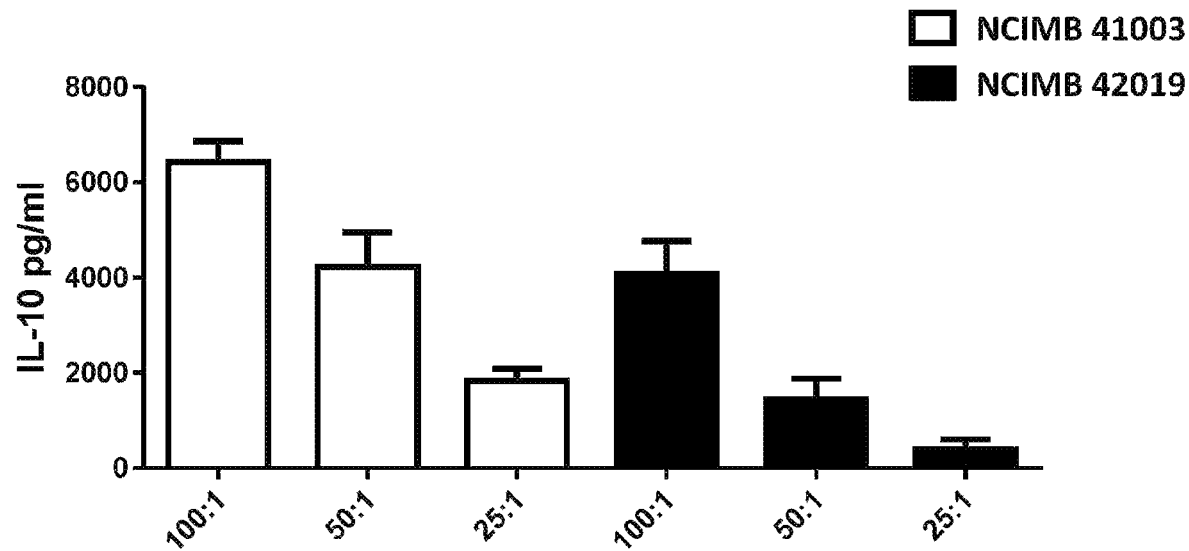
FIG. 6 is a chart of IL-10 induction in the PBMC cytokine induction assay following 48 h stimulation with *B. longum* NCIMB 41003 and *L. casei* NCIMB 42019. There is a slight increase in the anti-inflammatory cytokine IL-10 induction following stimulation with *B. longum* NCIMB 41003 relative to *L. casei* NCIMB 42019.

FIG. 6: IL-10 induction in the PBMC cytokine induction assay following 48 h stimulation with *B. longum* NCIMB 41003 and *L. casei* NCIMB 42019. There is a slight increase in the anti-inflammatory cytokine IL-10 induction following stimulation with *B. longum* NCIMB 41003 relative to *L. casei* NCIMB 42019.

Figure 7:
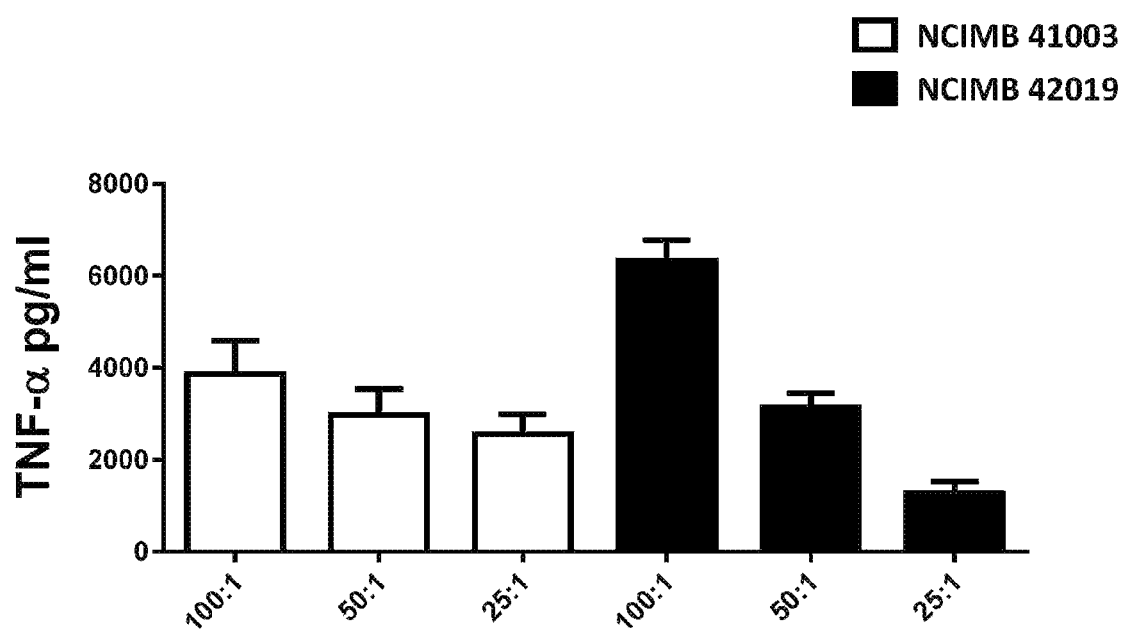
FIG. 7 is a chart of TNF-α induction in the PBMC cytokine induction assay following 48 h stimulation with *B. longum* NCIMB 41003 and *L. casei* NCIMB 42019. There is an increased TNF-α induction following stimulation with *L. casei* NCIMB 42019 relative to *B. longum* NCIMB 41003.

FIG. 7: TNF-α induction in the PBMC cytokine induction assay following 48 h stimulation with *B. longum* NCIMB 41003 and *L. casei* NCIMB 42019. There is an increased TNF-α induction following stimulation with *L. casei* NCIMB 42019 relative to *B. longum* NCIMB 41003.

Conclusion

*L. casei* NCIMB 42019 and *B. longum* NCIMB 41003, which are EPS-rich, induce similar anti-inflammatory immune profiles in a PBMC cytokine induction assay. The low-EPS producing strain produces a very different immune profile.

Example 6—Effect of Administration of L. casei NCIMB 42019, an EPS Low Lactobacillus Strain, and B. longum NCIMB 41003 on Metabolic Outcomes in the Diet-Induced Obesity (DIO) Mouse Model Method
Animals 7 week old male C57BL/6JRccHsd mice (Harlan Laboratories, Netherlands) (72 mice, n=12 per group), randomized based on body weight, were maintained in a controlled environment with 22±3° C. temperature, 50±20% humidity, a light/dark cycle of 12 h each and 15-20 fresh air changes per hour. Mice were housed group wise (4 mice per cage) and autoclaved corncob was used as bedding material. Mice were received at 5 weeks of age and were quarantined for one week followed by acclimatization for one week prior to commencement of study. From Day 0 mice were fed, ad libitum, and mice in each cage were provided with 50 ml of plain sterile drinking water (groups 1 and 2; Table 1) or drinking water containing freeze-dried probiotic ($1\times10^9$ cfu/dose/day) via polycarbonate bottles fitted with stainless steel sipper tubes (groups 3, 4, 5 and 6; Table 1). Treatment continued for 16 weeks.

Experimental Design

Day 0 onwards, group 1 was fed with low fat diet (LFD) D12450 (10% kcal % fat, gamma irradiated; Research Diets Inc, USA) and the other five groups (groups 2 to 6) were fed with high fat diet (HFD) D12451 (45% kcal % fat, gamma irradiated; Research Diets Inc) for a period of 16 weeks. HFD feeding induced insulin resistance and obesity in animals which was characterized by increase in body weight and fasting blood glucose values. Group 1 and 2 were provided with plain sterile drinking water while groups 3, 4, 5 and 6 were provided with drinking water containing $1\times10^9$ cfu/dose/day of the appropriate probiotic (Table 1). General health observation was performed on a daily basis at the same time of the day. This included alertness, hair texture, cage movement and presence of any discharge from nose, eyes, mouth and ears. Pre-measured feed was kept in each cage and the left over feed was measured and recorded on every third day to access the amount of food consumed by the mice. Water consumption of the animals was measured on a daily basis starting from the first dosing day. Mice in each cage (n=4) were provided with 50 mL of water daily. The remaining water in each cage was measured every 24 h.

Weights and Tissue Sampling

Body weights were recorded individually for all animals at receipt, day of randomization, prior to treatment, and once in three days thereafter. The percent change in bodyweight was calculated according to the formula (TT−TC)/TC*100 where TT is the test day treated and TC is the test day control. Mice were subjected to Echo Magnetic Resonance Imaging (MRI) using an Echo MRI (EchoMRI-700™) on day −1 and 28, 56, 84 and 112 to assess body fat and lean mass composition. The animal was placed in a plastic holder without sedation or anaesthesia. Fat is measured as the mass of all the fat molecules in the body. Lean is a muscle tissue mass equivalent of all the body parts containing water. Contribution to "free water" comes mostly from the bladder. Total water includes both the free water and the water contained in lean mass, which is the entire water content of the body. Plastic holders were sanitized between animals from different groups to avoid cross-contamination. Aseptic technique was followed while handling animals from different groups. At the end of week 16, the animals were sacrificed by $CO_2$ asphyxiation. Liver, skeletal muscle, visceral fat (epididymal, renal and mesenteric), subcutaneous fat, spleen, caecum, brown adipose fat, brain and intestine were collected, weighed and stored at −80° C. for future biochemical and genetic analysis.

Metabolic Markers

Blood samples were collected at morning 9 am by the tail nipping method on day 0, 30, 60, 90 and 112 for random blood glucose measurements (total 5 samplings were done), starting/including the first dosing day. Blood glucose analysis was done by Johnson and Johnson glucometer (One touch Ultra 2). Aseptic technique was followed while handling animals from different groups. At the end of 16 weeks, mice were fasted for 6 h and blood was collected by the tail nipping method (non-anesthetic mode of blood collection) for blood glucose estimation. Blood was collected by retro-orbital puncture method under light isoflurane anesthesia and plasma was separated which was used for estimating total cholesterol (TC), triglycerides (TG), high-density lipoprotein (HDL) cholesterol, low-density lipoprotein (LDL) cholesterol and non-esterified fatty acids (NEFA) by fully automated random access clinical chemistry analyzer (EM-360, Erba Mannheim, Germany). Plasma VLDL levels were obtained by the calculation method: (VLDL=Triglycerides (mg/dl)/5). For hepatic TC and TG estimation, liver was homogenized in isopropanol (1 ml/50 mg tissue) and incubated at 4° C. for 1 h. The samples were centrifuged at 4° C. for 5 min at 2,500 rpm. Cholesterol and triglyceride concentrations in the supernatants were measured by a fully automated random access clinical chemistry analyzer (EM-360, Erba Mannheim).

Gene Expression Analysis

The expression of genes involved in the regulation and enzymatic pathways of fatty acid metabolism and inflammation were analysed. Total RNA was prepared from liver samples using RNeasy Mini Kit (QIAgen, Germany). cDNA was prepared by reverse transcription of 1 µg total RNA using Reverse Transcription System Kit (QIAgen). cDNA from each group was pooled and was screened for each pooled cDNA sample using the Mouse Fatty Acid Metabolism $RT^2$ Profiler PCR Array (QIAgen) according to manufacturer's instructions. Data analysis was performed using the QIAgen $RT^2$ Profiler PCR Array accompanying online software. Data is presented as change in fold regulation of low-fat diet control versus high-fat diet control and change in fold regulation of probiotics versus high-fat diet control. A cut-off of below 2-fold regulation was considered as no change.

Energy Excretion Estimation

Two faecal pellets were collected from each mouse at Weeks 6, 10 and 15 and analyzed for their gross calorific value by bomb calorimetry. For bomb calorimetry analysis, the samples were weighed and oven-dried at 60° C. for 48 h. The energy content of the faeces was assessed with a Parr 6100 calorimeter using an 1109 semi-micro bomb (Parr Instruments & Co., Moline, Ill., USA). The calorimeter energy equivalent factor was determined using benzoic acid standards and each sample (100 mg) was analysed in triplicate. Cumulative energy excretion of probiotic fed mice over the course of the study was estimated as a percentage relative to energy excreted by mice from the high-fat diet control group.

Fat Excretion Estimation

Two faecal pellets were collected from each mouse at Weeks 0, 6, 10 and 14 and stored at −80° C. until further analysis. Faecal fat content was determined according to a modified method of Folch et al (Folch et al., 1957, Kraus, 2015). Faecal samples were weighed in 15 ml conical polypropylene tubes (Sarstedt) and deionized water (10× v/w) was added. Samples were vortexed for 60 seconds at high speed at soaked overnight at room temperature. To extract lipids 4× volume of chloroform and methanol mixture (2:1, v:v) to deionised water was added and vortexed for 60 seconds at high speed. The mixture was then centrifuged at 2000 g for 10 min. The bottom lipophilic layer from the extraction was collected by insertion of a 22G 1½ hypodermic needle (BD) through the tube wall and drained into pre-weighed tubes. The collected lipophilic layer was allowed to dry overnight. Total fat content was weighed using an analytical laboratory balance (Sartorius). Cumulative fat excretion of probiotic fed mice over the course of the study was estimated as a percentage relative to fat excreted by mice from the high-fat diet control group.

Statistical Analysis

Statistical analysis was performed using unpaired t-test for differences between two groups. One-way analysis of variance (ANOVA), followed by Tukey's multiple comparison test was used when more than two groups were assessed. Data were analyzed using GraphPad Prism version 5.00 for Windows (GraphPad Software). The results were considered statistically significant when $p<0.05$.

TABLE 5

Experimental groups and associated diet and treatment regimens.
LFD = Low fat diet control; HFD = high-fat diet control.

| Groups | Number of mice/ group | Diet regimen | Treatment regimen |
| --- | --- | --- | --- |
| Group 1 (LFD control) | 12 | 10% fat kcal | Plain sterile drinking water, daily |
| Group 2 (HFD control) | 12 | 45% fat kcal | Plain sterile drinking water, daily |
| Group 3 (HFD + L. casei NCIMB 42019) | 12 | 45% fat kcal | $1 \times 10^9$ cfu/dose/day in drinking water, daily |
| Group 4 (HFD + EPS low Lactobacillus strain) | 12 | 45% fat kcal | $1 \times 10^9$ cfu/dose/day in drinking water, daily |
| Group 6 (HFD + B. longum NCIMB 41003) | 12 | 45% fat kcal | $1 \times 10^9$ cfu/dose/day in drinking water, daily |

Results

Figure 8:
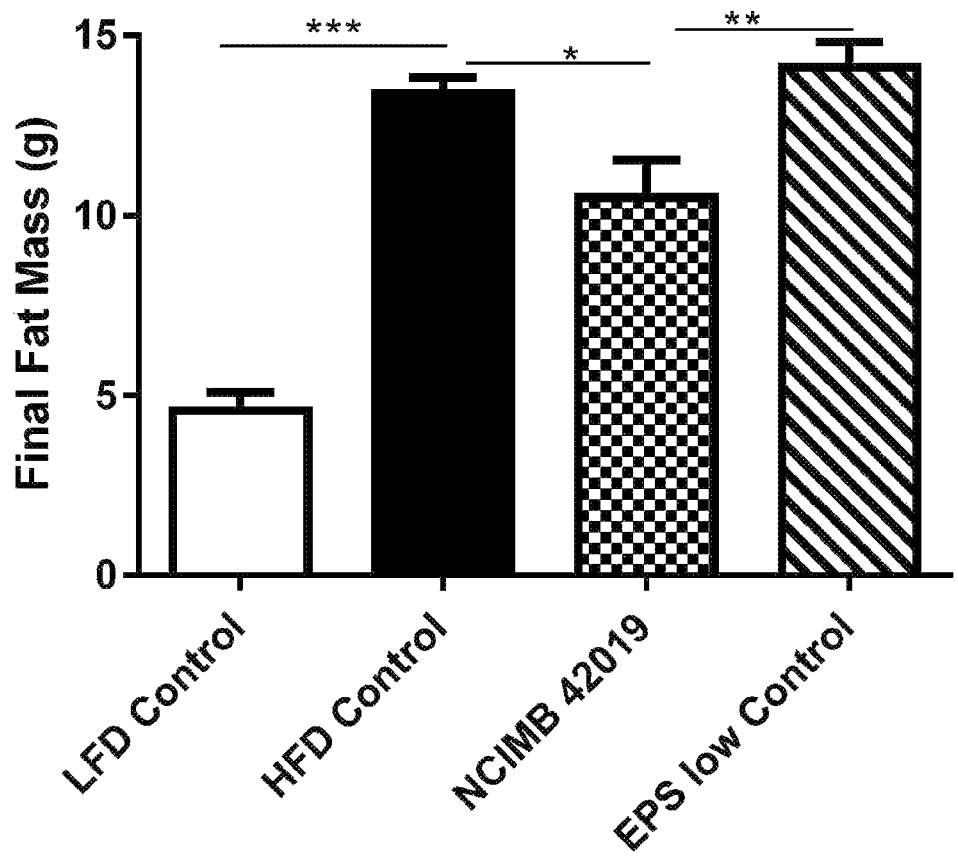
FIG. 8 illustrates that when compared to the high-fat diet (HFD) control group, *L. casei* NCIMB 42019 showed a significant reduction in reduction fat mass gain by week 16 while the EPS low *Lactobacillus* strain had no significant effect.

FIG. 8: When compared to the high-fat diet (HFD) control group, L. casei NCIMB 42019 showed a significant reduction in reduction fat mass gain by week 16 while the EPS low Lactobacillus strain had no significant effect.

Figure 9:
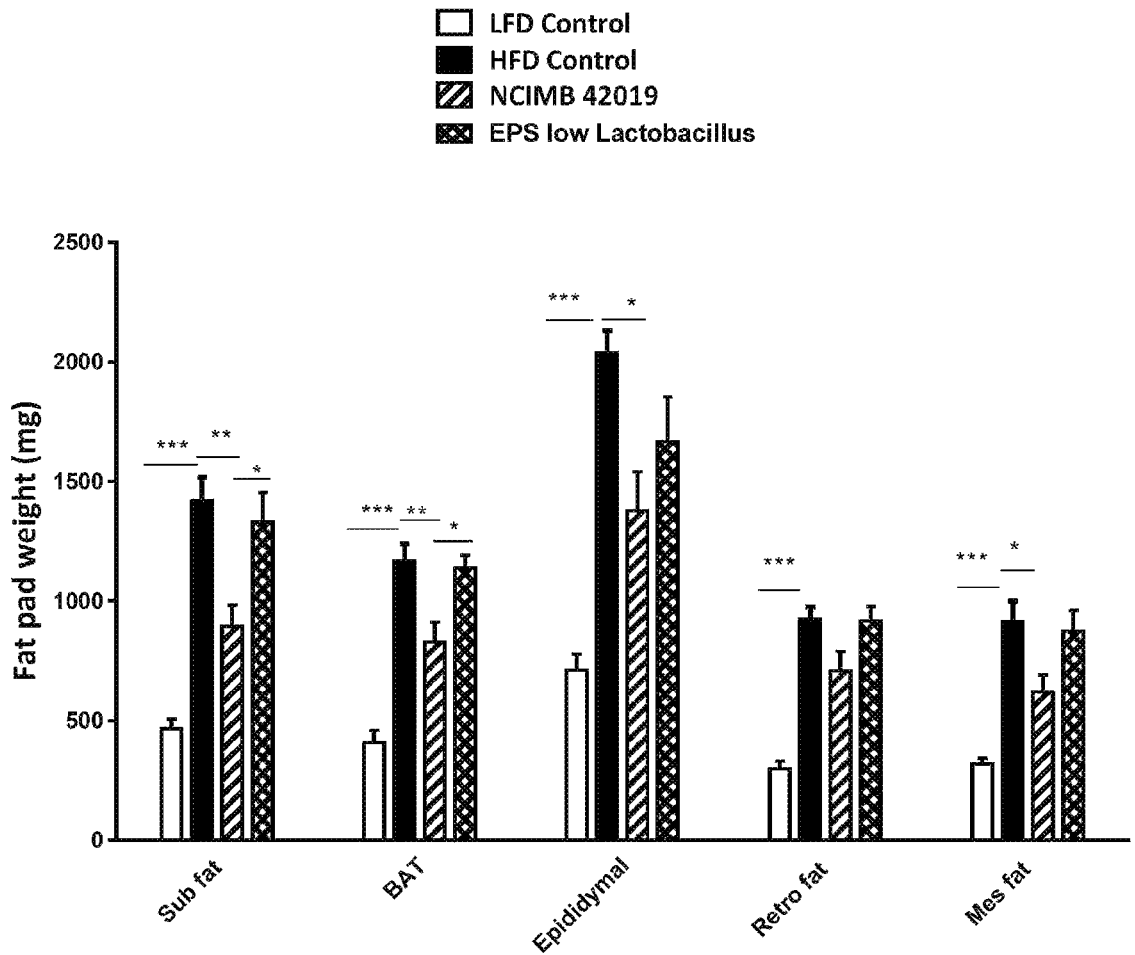
FIG. 9 shows the effect of *L. casei* NCIMB 42019 and an EPS low *Lactobacillus* strain on fat pad weight. *L. casei* NCIMB 42019 had a significant reduction in fat pad weights (subcutaneous fat, brown adipose tissue (BAT) and epipidymal fat) while the EPS low *Lactobacillus* strain had no significant effect.

FIG. 9: Effect of L. casei NCIMB 42019 and an EPS low Lactobacillus strain on fat pad weight. L. casei NCIMB 42019 had a significant reduction in fat pad weights (subcutaneous fat, brown adipose tissue (BAT) and epipidymal fat) while the EPS low Lactobacillus strain had no significant effect.

Figure 10:
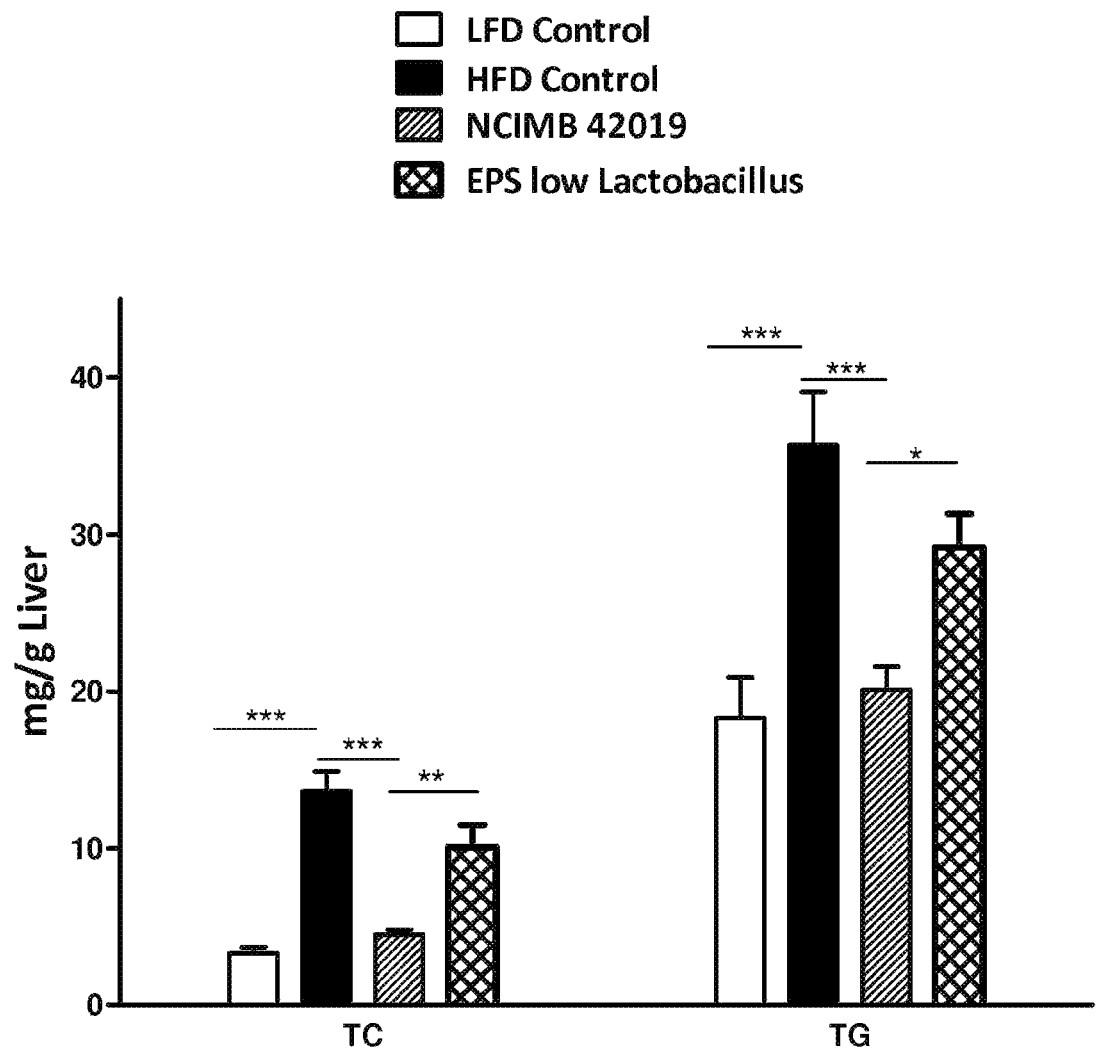
FIG. 10 illustrates the effect of *L. casei* NCIMB 42019 and an EPS low *Lactobacillus* strain on hepatic total cholesterol and triglycerides. *L. casei* NCIMB 42019 but not the EPS low *Lactobacillus* strain reduced hepatic total cholesterol and triglycerides in DIO mice.

FIG. 10: Effect of L. casei NCIMB 42019 and an EPS low Lactobacillus strain on hepatic total cholesterol and triglycerides. L. casei NCIMB 42019 but not the EPS low Lactobacillus strain reduced hepatic total cholesterol and triglycerides in DIO mice.

Figure 11:
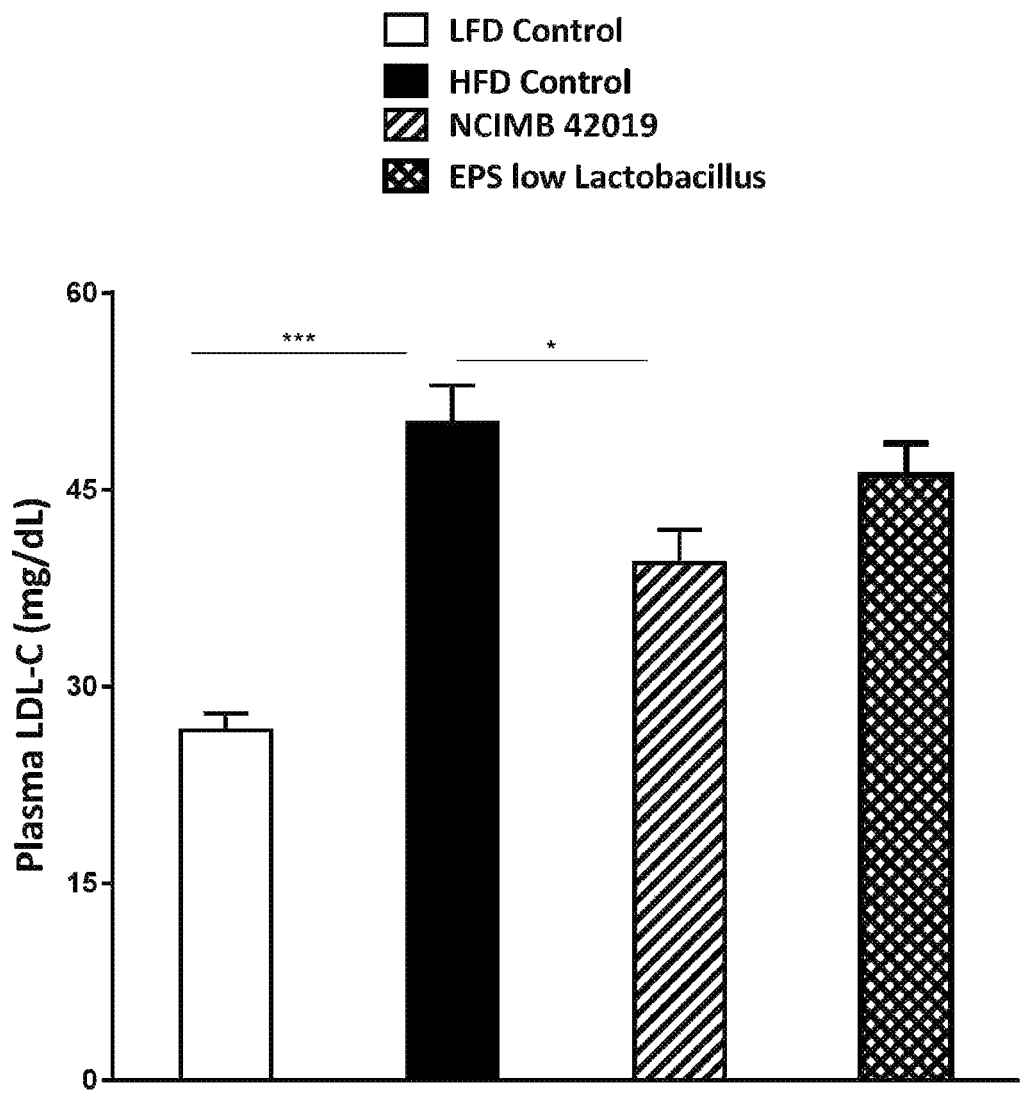
FIG. 11 illustrates the effect of *L. casei* NCIMB 42019 and an EPS low *Lactobacillus* strain on plasma LDL-cholesterol.

FIG. 11: Effect of L. casei NCIMB 42019 and an EPS low Lactobacillus strain on plasma LDL-cholesterol.

Figure 12:
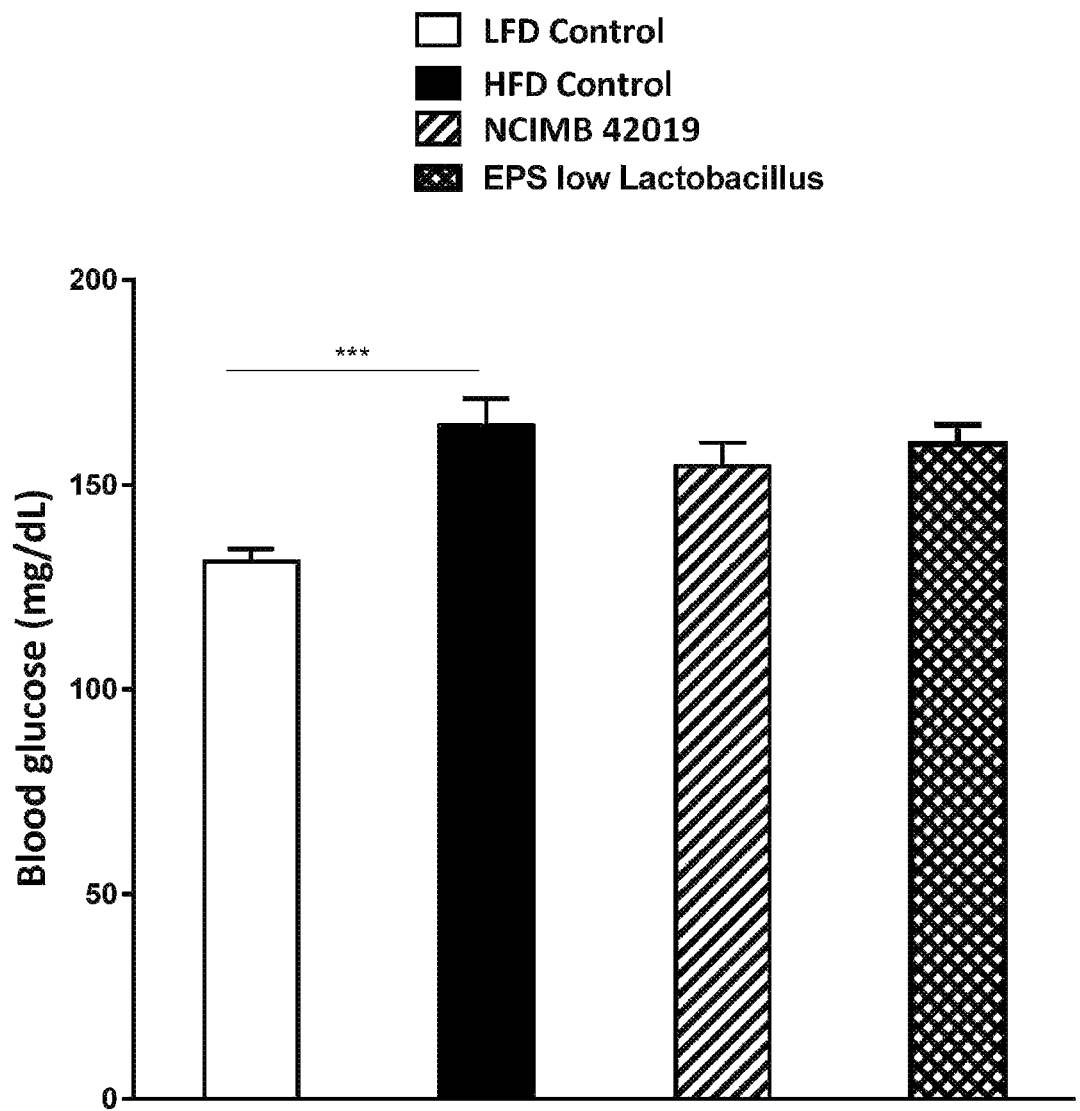
FIG. 12 illustrates the effect of *L. casei* NCIMB 42019 and an EPS low *Lactobacillus* strain on terminal blood glucose.

FIG. 12: Effect of L. casei NCIMB 42019 and an EPS low Lactobacillus strain on terminal blood glucose.

Figure 13:
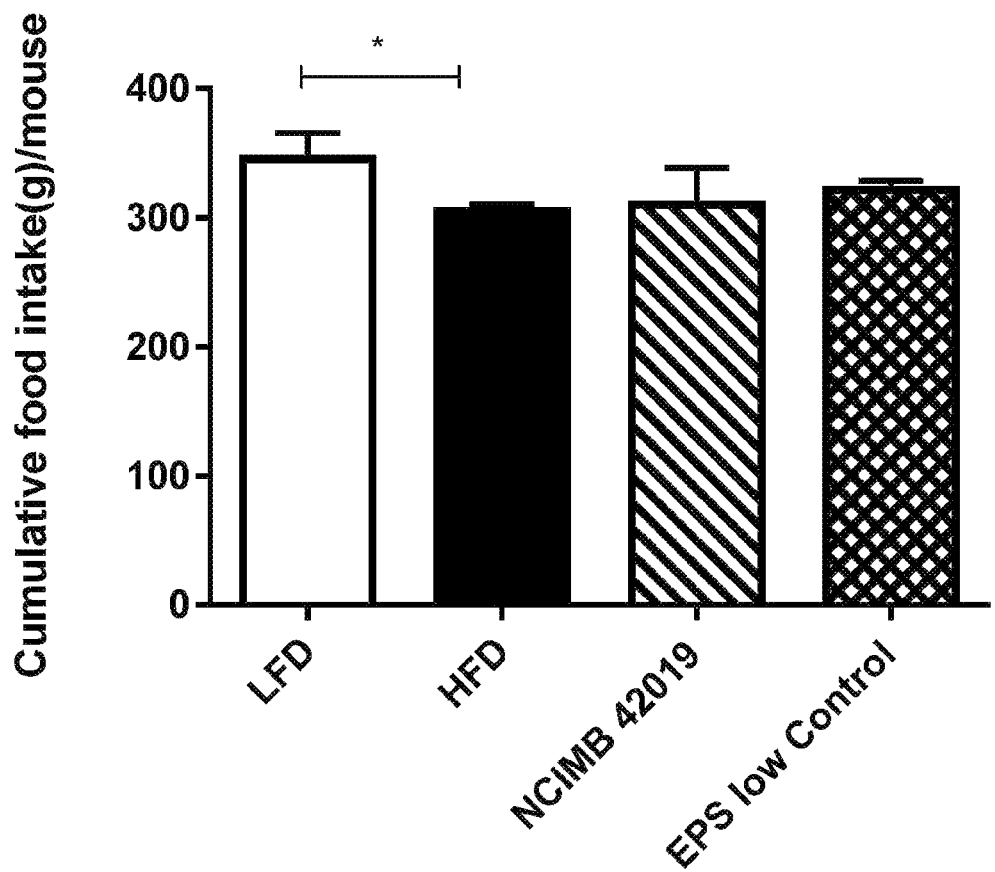
FIG. 13 plots the cumulative food intake per mouse following *L. casei* NCIMB 42019 and an EPS low *Lactobacillus* strain administration relative to the high-fat diet (HFD) control group in the DIO mouse model.

FIG. 13: Cumulative food intake per mouse following L. casei NCIMB 42019 and an EPS low Lactobacillus strain administration relative to the high-fat diet (HFD) control group in the DIO mouse model.

Figure 14:
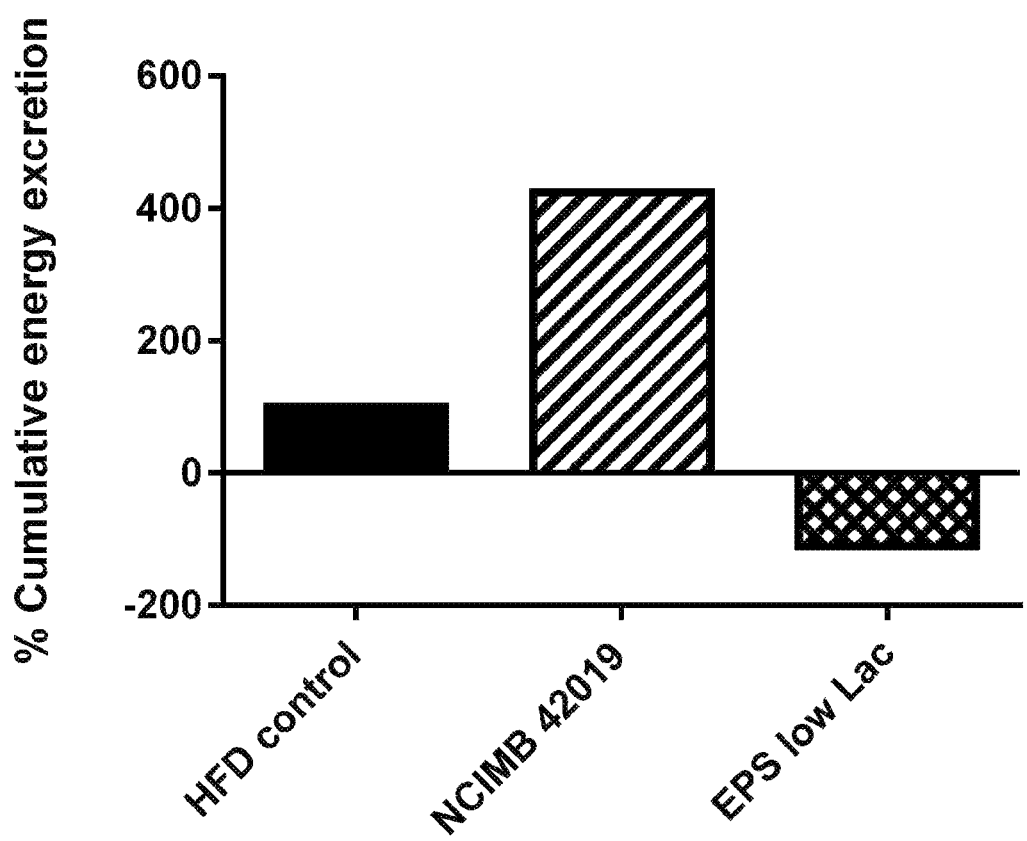
FIG. 14 presents the estimation of % cumulative energy excretion following *L. casei* NCIMB 42019 and an EPS low *Lactobacillus* strain administration relative to the high-fat diet (HFD) control group in the DIO mouse model.

FIG. 14: Estimation of % cumulative energy excretion following L. casei NCIMB 42019 and an EPS low Lactobacillus strain administration relative to the high-fat diet (HFD) control group in the DIO mouse model.

Figure 15A:
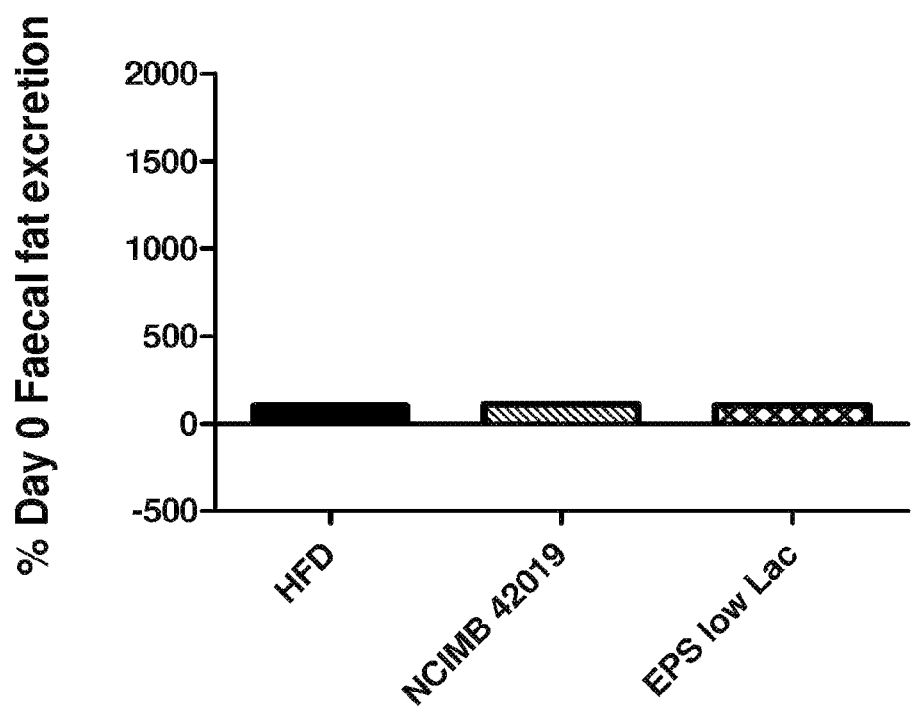
FIG. 15(a) shows no significant difference in faecal fat excretion/mouse/gram on Day 0, while (b) presents the estimation of % cumulative fat excretion following *L. casei* NCIMB 42019 and an EPS low *Lactobacillus* strain administration relative to the high-fat diet (HFD) control group in the DIO mouse model.
Figure 15B:
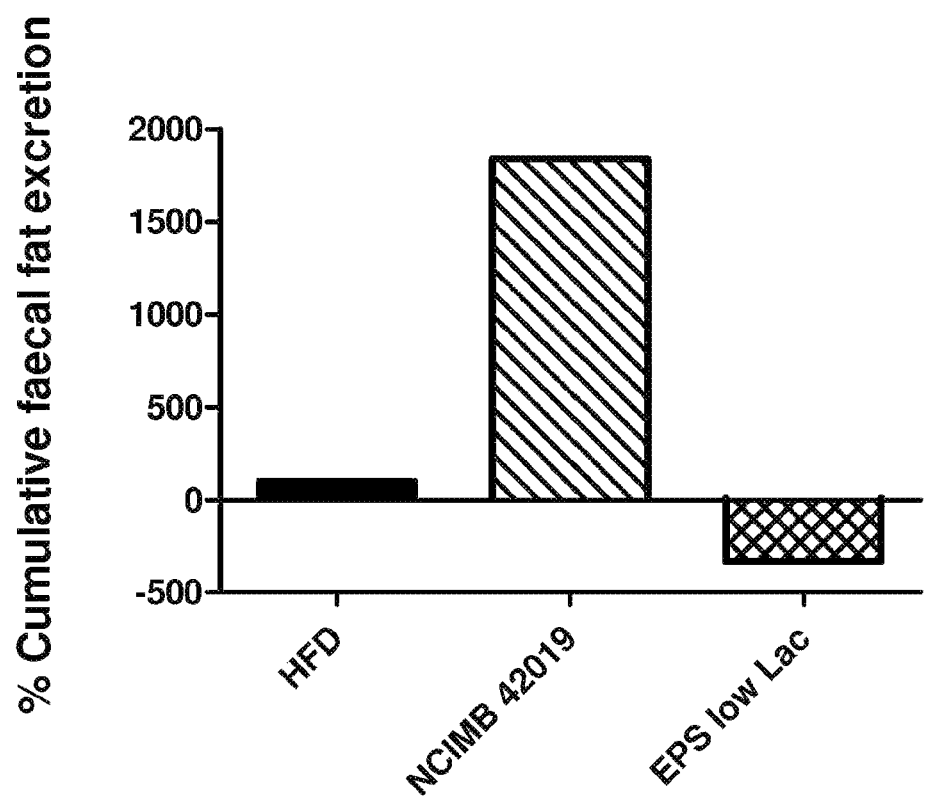

FIG. 15: Day 0 faecal fat excretion/mouse/gram. There was no significant difference in faecal fat excretion between groups on Day 0.

Figure 16:
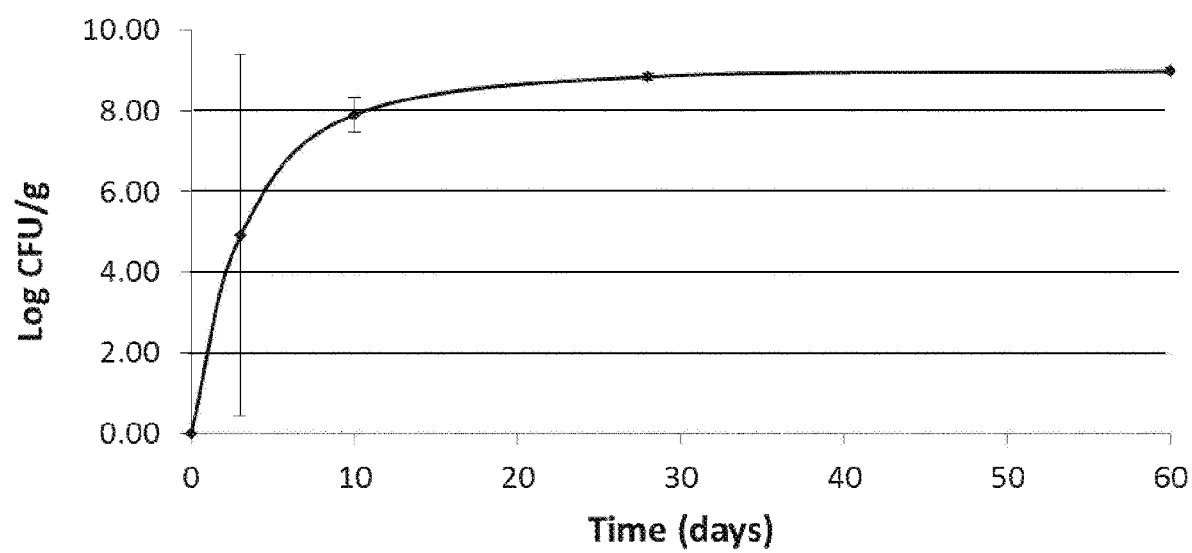
FIG. 16 shows the transit of *L. casei* NCIMB 42019 to high numbers in mice.

FIG. 16: Estimation of % cumulative fat excretion following L. casei NCIMB 42019 and an EPS low Lactobacillus strain administration relative to the high-fat diet (HFD) control group in the DIO mouse model.

TABLE 6

Expression profiles for genes involved in the regulation and enzymatic pathways of fatty acid metabolism and inflammation. L. casei NCIMB 42019 down-regulates genes associated with cholesterol metabolism and transport, adipokine signalling, β-oxidation and oxidative phosphorylation in a strain-specific manner. L. casei NCIMB 42019 up-regulates the anti-inflammatory cytokine Il-10 and down-regulates pro-inflammatory cytokine TNFα, independent of diet, in a strain-specific manner.

| Gene Function | Gene Symbol | Gene Info | LFD versus HFD (Fold Regulation) | HFD versus NCIMB 42019 (ΔFold Regulation) | HFD versus low EPS Lac (ΔFold Regulation) |
| --- | --- | --- | --- | --- | --- |
| CHOLESTEROL METABOLISM/ TRANSPORT | Cyp2e1 | Cytochrome P450, family 2, subfamily e, polypeptide 1 | +5.063 | −2.5663 | NC |
| | Cyp7a1 | Cytochrome P450, family 7, subfamily a, polypeptide 1 | +4.1989 | −3.4928 | NC |
| | Abcg1 | ATP-binding cassette, sub-family G (WHITE), member 1 | NC | −4.1894 | NC |
| | Srebf2 | sterol regulatory element binding transcription factor 2 | NC | −2.9725 | NC |
| | Abca1 | ATP-binding cassette, sub-family A (ABC1), member 1; CERP, cholesterol efflux regulatory protein | NC | −2.5967 | NC |
| | Nr1h4 | nuclear receptor subfamily 1, group H, member 4; bile acid receptor | NC | −2.4079 | NC |
| ADIPOKINE SIGNALLING | Scl2a4 | Solute carrier family 2 (facilitated glucose transporter), member 4; GLUT4 | −2.0279 | −8.3109 | NC |
| | Serpine1 | Serine (or cysteine) peptidase inhibitor, clade E, member 1 | −2.9282 | −8.3074 | NC |
| | Adipor1 | Adiponectin receptor 1 | NC | −2.9511 | NC |

TABLE 6-continued

Expression profiles for genes involved in the regulation and enzymatic pathways of fatty acid metabolism and inflammation. *L. casei* NCIMB 42019 down-regulates genes associated with cholesterol metabolism and transport, adipokine signalling, β-oxidation and oxidative phosphorylation in a strain-specific manner. *L. casei* NCIMB 42019 up-regulates the anti-inflammatory cytokine Il-10 and down-regulates pro-inflammatory cytokine TNFα, independent of diet, in a strain-specific manner.

| Gene Function | Gene Symbol | Gene Info | LFD versus HFD (Fold Regulation) | HFD versus NCIMB 42019 (ΔFold Regulation) | HFD versus low EPS Lac (ΔFold Regulation) |
|---|---|---|---|---|---|
| | Slc2a1 | Solute carrier family 2 (facilitated glucose transporter), member 1; GLUT1 | NC | −2.8817 | NC |
| | Tnf | Fas (TNF receptor superfamily member 6) | NC | −2.8524 | NC |
| | Akt1 | Thymoma viral proto-oncogene 1 | NC | −2.2818 | NC |
| OTHER LIPID METABOLISM TRANSPORT | Slc27a5 | Solute carrier family 27 (fatty acid transporter), member 5 | NC | −2.9246 | NC |
| β-OXIDATION | Fabp1 | Fatty acid-binding protein 1 | NC | −3.3444 | NC |
| | Akt1 | Thymoma viral proto-oncogene 1 | NC | −2.2818 | NC |
| OXIDATIVE PHOSPHORYLATION | Ndufb6 | NADH dehydrogenase (ubiquinone) 1 beta subcomplex, 6 | NC | −2.7981 | NC |
| INFLAMMATORY RESPONSE | IL10 | Interleukin 10 | NC | +2.6867 | NC |
| | Tnf | Fas (TNF receptor superfamily member 6) | NC | −2.8524 | NC |

Expression profiles for genes involved in the regulation and enzymatic pathways of fatty acid metabolism and inflammation in the liver.
NC = No change (i.e. below cut-off of 2-fold regulation).
+ = Upregulation;
− = down regulation.

Surprisingly, the EPS producing *B. longum* NICMB 41003 strain did not have any significant effect in this model.

Conclusion

*L. casei* NCIMB 42019 administration led to a significant reduction in fat mass by week sixteen. This was accompanied by a statistically significant reduction in subcutaneous fat, brown adipose tissue and epididymal fat for *L. casei* NCIMB 42019. *L. casei* NCIMB 42019 administration led to a significant reduction in hepatic total cholesterol and triglyceride levels when compared to the HFD control group. *L. casei* NCIMB 42019 alters metabolic pathways altered in a strain-specific manner. Despite no significant difference in cumulative food intake over the course of the study, we observed an increase in % energy excretion for *L. casei* NCIMB 42019, which was accompanied with an increase in % fat excretion, suggesting that the administration of the fat-binding, hydrophobic *L. casei* NCIMB 42019 strain may reduce the amount of fat extracted from ingested food which could be responsible for the improvements in metabolic outcomes observed in this DIO mouse model.

Example 6—Transit of *L. casei* NCIMB 42019 Through the Gastro-Intestinal Tract In Vivo Method The ability of *L. casei* NCIMB 42019 to transit in vivo was demonstrated in mice assessed in seven-week old male C57BL/J6 mice over a period of 60 days (n=5). *L. casei* NCIMB 42019 was delivered in drinking water at a daily concentration of $1\times10^9$ CFU/4 ml dose. Faecal samples were collected at 0, 3, 10, 28 and 60 days and *L. casei* NCIMB 42019 was recovered by plating onto MRS+rifampicin (50 ug/ml; Sigma-Aldrich).

Result

FIG. 16 shows *L. casei* NCIMB 42019 transits in high numbers in mice. *L. casei* NCIMB 42019 was detected in faeces by Day 3 at approximately $1\times10^5$ CFU/g. Detection had increased to approximately $1\times10^8$ CFU/g by Day 10 with levels reaching approximately $1\times10^9$ CFU/g by Day 28.

Conclusion

*L. casei* NCIMB 42019 transits to high numbers in vivo.

Prebiotics

The introduction of probiotic organisms is accomplished by the ingestion of the microorganism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

Formulations

One or more of the strains of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition, a vaccine comprising one or more of the strains of the invention may be prepared using any suitable known method and may include a pharmaceutically acceptable carrier or adjuvant.

The strains of the invention may be formulated to facilitate controlled release such as a delayed release of the strain. For example, the formulation may be adapted to release the strain at a particular location in the gastrointestinal tract such as the small intestine or in the colon. To achieve such a controlled release the strain may be formulated in a capsule which has a coating which is adapted to release the strain at a particular location. A range of coatings are available to facilitate such controlled release. One such family of coatings are those available under the Trade Mark Eudragit.

All documents cited herein are, in relevant part, incorporated herein by reference.

The invention is not limited to the embodiments hereinbefore described, which may be varied in detail.

REFERENCES

ADAMS, E. L., RICE, P. J., GRAVES, B., ENSLEY, H. E., YU, H., BROWN, G. D., GORDON, S., MONTEIRO, M. A., PAPP-SZABO, E., LOWMAN, D. W., POWER, T. D., WEMPE, M. F. & WILLIAMS, D. L. 2008. Differential high-affinity interaction of dectin-1 with natural or synthetic glucans is dependent upon primary structure and is influenced by polymer chain length and side-chain branching. *J Pharmacol Exp Ther*, 325, 115-23.

ARONSSON, L., HUANG, Y., PARINI, P., KORACH-ANDRE, M., HAKANSSON, J., GUSTAFSSON, J. A., PETTERSSON, S., ARULAMPALAM, V. & RAFTER, J. 2010. Decreased fat storage by *Lactobacillus paracasei* is associated with increased levels of angiopoietin-like 4 protein (ANGPTL4). *PLoS One*, 5.

BACKHED, F., DING, H., WANG, T., HOOPER, L. V., KOH, G. Y., NAGY, A., SEMENKOVICH, C. F. & GORDON, J. I. 2004. The gut microbiota as an environmental factor that regulates fat storage. *Proc Natl Acad Sci USA*, 101, 15718-23.

BACKHED, F., MANCHESTER, J. K., SEMENKOVICH, C. F. & GORDON, J. I. 2007. Mechanisms underlying the resistance to diet-induced obesity in germ-free mice. *Proc Natl Acad Sci USA*, 104, 979-84.

BLAND, E. J., KESHAVARZ, T. & BUCKE, C. 2004. The influence of small oligosaccharides on the immune system. *Carbohydr Res*, 339, 1673-8.

CANI, P. D., AMAR, J., IGLESIAS, M. A., POGGI, M., KNAUF, C., BASTELICA, D., NEYRINCK, A. M., FAVA, F., TUOHY, K. M., CHABO, C., WAGET, A., DELMEE, E., COUSIN, B., SULPICE, T., CHAMONTIN, B., FERRIERES, J., TANTI, J. F., GIBSON, G. R., CASTEILLA, L., DELZENNE, N. M., ALESSI, M. C. & BURCELIN, R. 2007. Metabolic endotoxemia initiates obesity and insulin resistance. *Diabetes*, 56, 1761-72.

CANI, P. D., BIBILONI, R., KNAUF, C., WAGET, A., NEYRINCK, A. M., DELZENNE, N. M. & BURCELIN, R. 2008a. Changes in gut microbiota control metabolic endotoxemia-induced inflammation in high-fat diet-induced obesity and diabetes in mice. *Diabetes*, 57, 1470-81.

CANI, P. D., DELZENNE, N. M., AMAR, J. & BURCELIN, R. 2008b. Role of gut microflora in the development of obesity and insulin resistance following high-fat diet feeding. *Pathol Biol (Paris)*, 56, 305-9.

FANNING, S., HALL, L. J., CRONIN, M., ZOMER, A., MACSHARRY, J., GOULDING, D., MOTHERWAY, M. O., SHANAHAN, F., NALLY, K., DOUGAN, G. & VAN SINDEREN, D. 2012. Bifidobacterial surface-exopolysaccharide facilitates commensal-host interaction through immune modulation and pathogen protection. *Proc Natl Acad Sci USA*, 109, 2108-13.

FOLCH, J., LEES, M. & SLOANE STANLEY, G. H. 1957. A simple method for the isolation and purification of total lipides from animal tissues. *J Biol Chem*, 226, 497-509.

GUH, D. P., ZHANG, W., BANSBACK, N., AMARSI, Z., BIRMINGHAM, C. L. & ANIS, A. H. 2009. The incidence of co-morbidities related to obesity and overweight: a systematic review and meta-analysis. *BMC Public Health*, 9, 88.

GUPTA, S., RICHARD, L. & FORSYTHE, A. 2015. The humanistic and economic burden associated with increasing body mass index in the EUS. *Diabetes Metab Syndr Obes*, 8, 327-38.

HIDALGO-CANTABRANA, C., LÓPEZ, P., GUEIMONDE, M., DE LOS REYES-GAVILÁN, C., SUÁREZ, A., MARGOLLES, A. & RUAS-MADIEDO, P. 2012. Immune Modulation Capability of Exopolysaccharides Synthesised by Lactic Acid Bacteria and Bifidobacteria. *Probiotics and Antimicrobial Proteins*, 4, 227-237.

HIDALGO-CANTABRANA, C., NIKOLIC, M., LOPEZ, P., SUAREZ, A., MILJKOVIC, M., KOJIC, M., MARGOLLES, A., GOLIC, N. & RUAS-MADIEDO, P. 2014. Exopolysaccharide-producing *Bifidobacterium animalis* subsp. *lactis* strains and their polymers elicit different responses on immune cells from blood and gut associated lymphoid tissue. *Anaerobe*, 26, 24-30.

JONES, S. E., PAYNICH, M. L., KEARNS, D. B. & KNIGHT, K. L. 2014. Protection from intestinal inflammation by bacterial exopolysaccharides. *J Immunol*, 192, 4813-20.

KAHN, S. E., HULL, R. L. & UTZSCHNEIDER, K. M. 2006. Mechanisms linking obesity to insulin resistance and type 2 diabetes. *Nature*, 444, 840-6.

KANKAINEN, M., PAULIN, L., TYNKKYNEN, S., VON OSSOWSKI, I., REUNANEN, J., PARTANEN, P., SATOKARI, R., VESTERLUND, S., HENDRICKX, A. P., LEBEER, S., DE KEERSMAECKER, S. C., VANDERLEYDEN, J., HAMALAINEN, T., LAUKKANEN, S., SALOVUORI, N., RITARI, J., ALATALO, E., KORPELA, R., MATTILA-SANDHOLM, T., LASSIG, A., HATAKKA, K., KINNUNEN, K. T., KARJALAINEN, H., SAXELIN, M., LAAKSO, K., SURAKKA, A., PALVA, A., SALUSJARVI, T., AUVINEN, P. & DE VOS, W. M. 2009. Comparative genomic analysis of *Lactobacillus rhamnosus* GG reveals pili containing a human-mucus binding protein. *Proc Natl Acad Sci USA*, 106, 17193-8.

KOTZAMPASSI, K., GIAMARELLOS-BOURBOULIS, E. J. & STAVROU, G. 2014. Obesity as a consequence of gut bacteria and diet interactions. *ISRN Obes*, 2014, 651895.

KRAUS, D., YANG, Q. AND KAHN, B. B. 2015. Lipid Extraction from Mouse Feces. Bio-protocol, 5, e1375.

LEE, H. Y., PARK, J. H., SEOK, S. H., BAEK, M. W., KIM, D. J., LEE, K. E., PAEK, K. S., LEE, Y. & PARK, J. H. 2006. Human originated bacteria, *Lactobacillus rhamnosus* PL60, produce conjugated linoleic acid and show anti-obesity effects in diet-induced obese mice. *Biochim Biophys Acta*, 1761, 736-44.

NAITO, E., YOSHIDA, Y., MAKINO, K., KOUNOSHI, Y., KUNIHIRO, S., TAKAHASHI, R., MATSUZAKI, T., MIYAZAKI, K. & ISHIKAWA, F. 2011. Beneficial effect of oral administration of *Lactobacillus casei* strain Shirota on insulin resistance in diet-induced obesity mice. *J Appl Microbiol,* 110, 650-7.

RIDAURA, V. K., FAITH, J. J., REY, F. E., CHENG, J., DUNCAN, A. E., KAU, A. L., GRIFFIN, N. W., LOMBARD, V., HENRISSAT, B., BAIN, J. R., MUEHLBAUER, M. J., ILKAYEVA, O., SEMENKOVICH, C. F., FUNAI, K., HAYASHI, D. K., LYLE, B. J., MARTINI, M. C., URSELL, L. K., CLEMENTE, J. C., VAN TREUREN, W., WALTERS, W. A., KNIGHT, R., NEWGARD, C. B., HEATH, A. C. & GORDON, J. I. 2013. Gut microbiota from twins discordant for obesity modulate metabolism in mice. *Science,* 341, 1241214.

TURNBAUGH, P. J., HAMADY, M., YATSUNENKO, T., CANTAREL, B. L., DUNCAN, A., LEY, R. E., SOGIN, M. L., JONES, W. J., ROE, B. A., AFFOURTIT, J. P., EGHOLM, M., HENRISSAT, B., HEATH, A. C., KNIGHT, R. & GORDON, J. I. 2009. A core gut microbiome in obese and lean twins. *Nature,* 457, 480-4.

TURNBAUGH, P. J., LEY, R. E., MAHOWALD, M. A., MAGRINI, V., MARDIS, E. R. & GORDON, J. I. 2006. An obesity-associated gut microbiome with increased capacity for energy harvest. *Nature,* 444, 1027-31.

VINDEROLA, G., PERDIGON, G., DUARTE, J., FARNWORTH, E. & MATAR, C. 2006. Effects of the oral administration of the exopolysaccharide produced by *Lactobacillus* kefiranofaciens on the gut mucosal immunity. *Cytokine,* 36, 254-60.

VOLMAN, J. J., RAMAKERS, J. D. & PLAT, J. 2008. Dietary modulation of immune function by beta-glucans. *Physiol Behav,* 94, 276-84.

VRIEZE, A., VAN NOOD, E., HOLLEMAN, F., SALOJARVI, J., KOOTTE, R. S., BARTELSMAN, J. F., DALLINGA-THIE, G. M., ACKERMANS, M. T., SERLIE, M. J., OOZEER, R., DERRIEN, M., DRUESNE, A., VAN HYLCKAMA VLIEG, J. E., BLOKS, V. W., GROEN, A. K., HEILIG, H. G., ZOETENDAL, E. G., STROES, E. S., DE VOS, W. M., HOEKSTRA, J. B. & NIEUWDORP, M. 2012. Transfer of intestinal microbiota from lean donors increases insulin sensitivity in individuals with metabolic syndrome. *Gastroenterology,* 143, 913-6.e7.

The invention claimed is:

1. A method for treating a health condition of a subject, the method comprising administering a formulation to the subject in need thereof, the formulation comprising an ingestible carrier and a therapeutically effective amount of *Lactobacillus casei* strain AH077 deposited with the National Collection of Industrial, Food and Marine Bacteria (NCIMB) under accession number 42019, wherein the health condition includes obesity, obesity-related metabolic syndrome, non-alcoholic fatty liver disease, or a combination thereof.

2. The method of claim 1, wherein the *Lactobacillus casei* strain is in the form of viable cells.

3. The method of claim 1, wherein the *Lactobacillus casei* strain is in the form of non-viable cells.

4. The method of claim 1, wherein the *Lactobacillus casei* strain is in the form of viable cells and non-viable cells.

5. The method of claim 1, wherein the formulation is in the form of a tablet or a powder.

6. The method of claim 1, wherein the formulation is in the form of a freeze-dried powder.

7. The method of claim 1, wherein the formulation is in the form of a food product.

8. The method of claim 1, wherein the formulation is in the form of a capsule or a sachet.

9. The method of claim 1, wherein the formulation further comprises a prebiotic.

10. The method of claim 1, wherein the formulation further comprises a protein, a peptide, or a combination thereof.

11. The method of claim 1, wherein the *Lactobacillus casei* strain is present in the formulation in an amount of more than $10^6$ cfu.

12. The method of claim 1, wherein the formulation further comprises an adjuvant.

13. The method of claim 1, wherein the formulation further comprises a drug entity or a biological compound.

14. The method of claim 1, wherein the subject is a human.

15. A method for treating a health condition, the method comprising administering a formulation to the subject in need thereof, the formulation comprising a therapeutically effective amount of *Lactobacillus casei* strain AH077 deposited with the National Collection of Industrial, Food and Marine Bacteria (NCIMB) under accession number 42019 and an ingestible carrier, wherein the ingestible carrier comprises a pharmaceutically acceptable carrier chosen from a capsule, a tablet, or a powder, and wherein the health condition is obesity, obesity-related metabolic syndrome, or non-alcoholic fatty liver disease.

16. The method of claim 15, wherein the *Lactobacillus casei* strain is in the form of viable cells, non-viable cells, or both.

17. The method of claim 15, wherein the formulation further comprises a prebiotic, a protein, a peptide, or a combination thereof.

18. The method of claim 15, wherein the *Lactobacillus casei* strain is present in the formulation in an amount of more than $10^6$ cfu.

19. The method of claim 15, wherein the formulation further comprises an adjuvant, a drug entity, or a biological compound.

20. The method of claim 15, wherein the subject is a human.

* * * * *